US005977298A

United States Patent [19]

[11] Patent Number: 5,977,298

[45] Date of Patent: Nov. 2, 1999

Shibata et al.

[54] CALCITONIN DERIVATIVES

[75] Inventors: Kenji Shibata, Kawasaki; Motoo Yamasaki, Machida; Masako Hamada, Tokyo; Tatsuya Tamaoki; Nobuo Kosaka, both of Sunto-gun; Soichiro Sato, Mishima, all of Japan

[73] Assignee: Kvowa Hakko Kogyo Co., Ltd., Tokyo, Japan

[21] Appl. No.: 08/934,741

[22] Filed: Sep. 22, 1997

Related U.S. Application Data

[63] Continuation of application No. 08/737,570, filed as application No. PCT/JP96/00666, Mar. 15, 1996, abandoned.

[30] Foreign Application Priority Data

Mar. 20, 1995 [JP] Japan ..................................... 7-61026

[51] Int. Cl.[6] ..................................................... A61K 38/00

[52] U.S. Cl. ............................. 530/307; 530/317; 930/60

[58] Field of Search ..................................... 530/307, 317; 930/60

[56] References Cited

U.S. PATENT DOCUMENTS 5,552,520 9/1996 Kim ....................................... 530/311

5,639,860 6/1997 Tanaka ................................... 530/326

OTHER PUBLICATIONS

Katahira et al., Bioorganic & Medical Chemistry 3(9):1273–80, 1995.

Morishita et al., The Journal of Antibiotics 47(3):269–275, Mar. 1994.

Yamasaki et al., The Journal of Antibiotics 47(3):276–80, Mar. 1994.

Karaki et al., European Journal of Pharmacology 262:255–59, Sep. 1994.

*Primary Examiner*—Lila Feisee

*Assistant Examiner*—Eliane Lazar-Wesley

*Attorney, Agent, or Firm*—Antonelli, Terry, Stout & Kraus, LLP

[57] ABSTRACT

The present invention relates to compounds represented by formula (I):

(I)

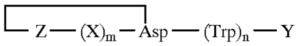

wherein Z represents Gly or Cys; X represents an (α-amino acid residue; Y represents a natural calcitonin moiety, a partial natural calcitonin peptide moiety, or a natural calcitonin-like peptide moiety; m represents an integer of 5–8, α-amino acid residues represented by X being the same or different; and n represents an integer of 0–3; provided that when m is 5, the sequence of 4 C-terminal residues of —$(X)_m$— is different from the sequence of the third to sixth amino acids of natural calcitonin, and pharmaceutically acceptable salts thereof.

3 Claims, 1 Drawing Sheet

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
(A) LENGTH: 34 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 34
(C) IDENTIFICATION METHOD: by experiment
(D) OTHER INFORMATION: /label= Xaa at location 34 /note= L-prolinamide (xi) SEQUENCE DESCRIPTION: SEQ ID NO:1:

```
Xaa Asn Trp His Gly Thr Ala Pro Xaa Trp Leu Gly Lys Leu Ser Gln
1               5                   10                  15

Glu Leu His Lys Leu Gln Thr Tyr Pro Arg Thr Asn Thr Gly Ser Gly
            20                  25                  30

Thr Xaa
```

(2) INFORMATION FOR SEQ ID NO:2:

(i) SEQUENCE CHARACTERISTICS:
(A) LENGTH: 34 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 34
(C) IDENTIFICATION METHOD: by experiment
(D) OTHER INFORMATION: /label= Xaa at location 34 /note= L-prolinamide (xi) SEQUENCE DESCRIPTION: SEQ ID NO:2:

```
Xaa Asn Trp His Gly Thr Ala Pro Xaa Val Leu Gly Lys Leu Ser Gln
1               5                   10                  15

Glu Leu His Lys Leu Gln Thr Tyr Pro Arg Thr Asn Thr Gly Ser Gly
            20                  25                  30

Thr Xaa
```

(2) INFORMATION FOR SEQ ID NO:3:

(i) SEQUENCE CHARACTERISTICS:
(A) LENGTH: 34 amino acids
(B) TYPE: amino acid
(C) STRANDEDNESS: single (D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 34
(C) IDENTIFICATION METHOD: by experiment
(D) OTHER INFORMATION: /label= Xaa at location 34 /note= L-prolinamide (xi) SEQUENCE DESCRIPTION: SEQ ID NO:3:

```
Xaa Asn Trp His Gly Thr Ala Pro Xaa Val Leu Ala Ala Leu Ala Ala
1               5                   10                  15

Ala Leu Ala Ala Leu Ala Ala Leu Pro Arg Thr Asn Thr Gly Ser Gly
            20                  25                  30

Thr Xaa
```

(2) INFORMATION FOR SEQ ID NO:4:

(i) SEQUENCE CHARACTERISTICS:
(A) LENGTH: 34 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 34
(C) IDENTIFICATION METHOD: by experiment
(D) OTHER INFORMATION: /label= Xaa at location 34 /note= L-prolinamide (xi) SEQUENCE DESCRIPTION: SEQ ID NO:4:

```
Xaa Asn Trp His Gly Thr Ala Pro Xaa Met Leu Gly Thr Tyr Thr Gln
1               5                   10                  15

Asp Phe Asn Lys Phe His Thr Phe Pro Gln Thr Ala Ile Gly Val Gly
            20                  25                  30

Ala Xaa
```

(2) INFORMATION FOR SEQ ID NO:5:

(i) SEQUENCE CHARACTERISTICS:
(A) LENGTH: 34 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 34
(C) IDENTIFICATION METHOD: by experiment
(D) OTHER INFORMATION: /label= Xaa at location 34

/note= L-prolinamide (xi) SEQUENCE DESCRIPTION: SEQ ID NO:5:

```
Xaa Asn Trp His Gly Thr Ala Pro Xaa Gly Leu Gly Ser Leu Thr Glu
1               5                   10                  15

Val Leu Ala Lys Leu Ala Ala Tyr Pro Arg Thr Asn Thr Gly Ser Gly
            20                  25                  30

Thr Xaa
```

(2) INFORMATION FOR SEQ ID NO:6:

(i) SEQUENCE CHARACTERISTICS:
(A) LENGTH: 34 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 34
(C) IDENTIFICATION METHOD: by experiment
(D) OTHER INFORMATION: /label= Xaa at location 34 /note= L-prolinamide (xi) SEQUENCE DESCRIPTION: SEQ ID NO:6:

```
Xaa Asn Trp His Gly Thr Ala Pro Xaa Gly Leu Gly Ser Leu Thr Glu
1               5                   10                  15

Val Leu Ala Lys Leu Ala Ala Tyr Pro Arg Ser Gln Thr Gly Ala Gly
            20                  25                  30

Thr Xaa
```

(2) INFORMATION FOR SEQ ID NO:7:

(i) SEQUENCE CHARACTERISTICS:
(A) LENGTH: 34 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 24
(C) IDENTIFICATION METHOD: by experiment
(D) OTHER INFORMATION: /label= Xaa at location 24 /note= trans-4-hydroxy-L-proline
(A) NAME/KEY: Modified-site
(B) LOCATION: 34
(C) IDENTIFICATION METHOD: by experiment
(D) OTHER INFORMATION: /label= Xaa at location 34 /note= trans-4-hydroxy-L-prolinamide (xi) SEQUENCE DESCRIPTION: SEQ ID NO:7:

```
Xaa Asn Trp His Gly Thr Ala Pro Xaa Gly Leu Gly Ser Leu Thr Glu
1               5                   10                  15

Val Leu Ala Lys Leu Ala Ala Tyr Xaa Arg Thr Asn Thr Gly Ser Gly
            20                  25                      30
```

Thr Xaa (2) INFORMATION FOR SEQ ID NO:8:

(i) SEQUENCE CHARACTERISTICS:
(A) LENGTH: 34 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 30
(C) IDENTIFICATION METHOD: by experiment
(D) OTHER INFORMATION: /label= Xaa at location 30 /note= b-alanine
(A) NAME/KEY: Modified-site
(B) LOCATION: 34
(C) IDENTIFICATION METHOD: by experiment
(D) OTHER INFORMATION: /label= Xaa at location 34 /note= L-prolinamide (xi) SEQUENCE DESCRIPTION: SEQ ID NO:8:

```
Xaa Asn Trp His Gly Thr Ala Pro Xaa Gly Leu Gly Ser Leu Thr Glu
1               5                   10                  15

Val Leu Ala Lys Leu Ala Ala Tyr Pro Arg Thr Asn Thr Xaa Ser Gly
            20                  25                  30

Thr Xaa
```

(2) INFORMATION FOR SEQ ID NO:9:

(i) SEQUENCE CHARACTERISTICS:
(A) LENGTH: 34 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 34
(C) IDENTIFICATION METHOD: by experiment
(D) OTHER INFORMATION: /label= Xaa at location 34 /note= trans-4-hydroxy-L-prolinamide (xi) SEQUENCE DESCRIPTION: SEQ ID NO:9:

```
Xaa Asn Trp His Gly Thr Ala Pro Xaa Gly Leu Gly Ser Leu Thr Glu
1               5                   10                  15

Val Leu Ala Lys Leu Ala Glu Tyr Pro Arg Thr Asn Thr Gly Ser Gly
                20                  25                  30

Thr Xaa
```

(2) INFORMATION FOR SEQ ID NO:10:

(i) SEQUENCE CHARACTERISTICS:
(A) LENGTH: 34 amino acids
(B) TYPE: amino acid

-continued (C) STRANDEDNESS: single
(D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 16
(C) IDENTIFICATION METHOD: by experiment
(D) OTHER INFORMATION: /label= Xaa at location 16 /note= g-carboxy-L-glutamic acid
(A) NAME/KEY: Modified-site
(B) LOCATION: 34
(C) IDENTIFICATION METHOD: by experiment
(D) OTHER INFORMATION: /label= Xaa at location 34 /note= L-prolinamide (xi) SEQUENCE DESCRIPTION: SEQ ID NO:10:

```
Xaa Asn Trp His Gly Thr Ala Pro Xaa Gly Leu Gly Ser Leu Thr Xaa
1               5                   10                  15

Val Leu Ala Lys Leu Ala Glu Tyr Pro Arg Thr Asn Thr Gly Ser Gly
            20                  25                  30

Thr Xaa
```

(2) INFORMATION FOR SEQ ID NO:11:

(i) SEQUENCE CHARACTERISTICS:
(A) LENGTH: 34 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 23
(C) IDENTIFICATION METHOD: by experiment
(D) OTHER INFORMATION: /label= Xaa at location 23 /note= g-carboxy-L-glutamic acid
(A) NAME/KEY: Modified-site
(B) LOCATION: 34
(C) IDENTIFICATION METHOD: by experiment
(D) OTHER INFORMATION: /label= Xaa at location 34 /note= L-prolinamide (xi) SEQUENCE DESCRIPTION: SEQ ID NO:11:

```
Xaa Asn Trp His Gly Thr Ala Pro Xaa Gly Leu Gly Ser Leu Thr Glu
1               5                   10                  15

Val Leu Ala Lys Leu Ala Xaa Tyr Pro Arg Thr Asn Thr Gly Ser Gly
            20                  25                  30

Thr Xaa
```

(2) INFORMATION FOR SEQ ID NO:12:

(i) SEQUENCE CHARACTERISTICS:
(A) LENGTH: 34 amino acids
(B) TYPE: amino acid
(C) STRANDEDNESS: single
(D) TOPOLOGY: linear (ii) MOLECULE TYPE: peptide -continued (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 34
(C) IDENTIFICATION METHOD: by experiment
(D) OTHER INFORMATION: /label= Xaa at location 34 /note= L-prolinamide (xi) SEQUENCE DESCRIPTION: SEQ ID NO:12:

```
Xaa Asn Trp His Gly Thr Ala Pro Xaa Gly Leu Gly Ser Leu Thr Xaa
1               5                   10                  15

Val Leu Ala Lys Leu Ala Glu Tyr Pro Lys Thr Asn Thr Gly Ser Gly
            20                  25                  30

Thr Xaa
```

(2) INFORMATION FOR SEQ ID NO:13:

(i) SEQUENCE CHARACTERISTICS:
(A) LENGTH: 34 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9

(xi) SEQUENCE DESCRIPTION: SEQ ID NO:13:

```
Xaa Asn Trp His Gly Thr Ala Pro Xaa Gly Leu Gly Ser Leu Thr Glu
1               5                   10                  15

Val Leu Ala Lys Leu Ala Glu Tyr Xaa Arg Thr Asn Thr Gly Ser Gly
            20                  25                  30

Thr Pro
```

(2) INFORMATION FOR SEQ ID NO:14:

(i) SEQUENCE CHARACTERISTICS:
(A) LENGTH: 34 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9

(xi) SEQUENCE DESCRIPTION: SEQ ID NO:14:

```
Xaa Asn Trp His Gly Thr Ala Pro Xaa Gly Leu Gly Ser Leu Thr Glu
1               5                   10                  15

Val Leu Ala Lys Leu Ala Glu Tyr Pro Lys Thr Asn Thr Gly Ser Gly
            20                  25                  30

Thr Pro
```

-continued (2) INFORMATION FOR SEQ ID NO:15:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 10
(C) IDENTIFICATION METHOD: by experiment
(D) OTHER INFORMATION: /label= Xaa at location 10 /note= L-tryptophan benzyl ester (xi) SEQUENCE DESCRIPTION: SEQ ID NO:15:

```
Xaa Asn Trp His Gly Thr Ala Pro Xaa Xaa
1               5                   10
```

(2) INFORMATION FOR SEQ ID NO:16:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(B) LOCATION: 1 and 9
(C) IDENTIFICATION METHOD: by experiment
(D) OTHER INFORMATION: /label= Xaa at location 1 is Gly crosslinked to Xaa which is Asp at location 9
(A) NAME/KEY: Modified-site
(B) LOCATION: 9
(C) IDENTIFICATION METHOD: by experiment
(D) OTHER INFORMATION: /label= Xaa at location 9 /note= L-aspartic acid b-t-butyl ester (xi) SEQUENCE DESCRIPTION: SEQ ID NO:16:

```
Xaa Asn Trp His Gly Thr Ala Pro Xaa
1               5
```

(2) INFORMATION FOR SEQ ID NO:17:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(C) IDENTIFICATION METHOD: by experiment
(D) OTHER INFORMATION: /label= Xaa at location 1 /note= Na-9-fluorenylmethyloxycarbonylglycine
(A) NAME/KEY: Modified-site
(B) LOCATION: 2
(C) IDENTIFICATION METHOD: by experiment
(D) OTHER INFORMATION: /label= Xaa at location 2 /note= Ng-trityl-L-asparagine
(A) NAME/KEY: Modified-site
(B) LOCATION: 4
(C) IDENTIFICATION METHOD: by experiment
(D) OTHER INFORMATION: /label= Xaa at location 4

/note= Nim-trityl-L-histidine
(A) NAME/KEY: Modified-site
(B) LOCATION: 6
(C) IDENTIFICATION METHOD: by experiment
(D) OTHER INFORMATION: /label= Xaa at location 6
/note= O-t-butyl-L-threonine
(A) NAME/KEY: Modified-site
(B) LOCATION: 9
(C) IDENTIFICATION METHOD: by experiment
(D) OTHER INFORMATION: /label= Xaa at location 9
/note= L-aspartic acid b-t-butyl ester
(A) NAME/KEY: Modified-site
(B) LOCATION: 10
(C) IDENTIFICATION METHOD: by experiment
(D) OTHER INFORMATION: /label= Xaa at location 10
/note= L-tryptophan benzyl ester (xi) SEQUENCE DESCRIPTION: SEQ ID NO:17:

```
Xaa Xaa Trp Xaa Gly Xaa Ala Pro Xaa Xaa
1               5                   10
```

(2) INFORMATION FOR SEQ ID NO:18:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 10
(C) IDENTIFICATION METHOD: by experiment
(D) OTHER INFORMATION: /label= Xaa at location 10
/note= L-tryptophan benzyl ester (xi) SEQUENCE DESCRIPTION: SEQ ID NO:18:

```
Gly Asn Trp His Gly Thr Ala Pro Asp Xaa
1               5                   10
```

(2) INFORMATION FOR SEQ ID NO:19:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(C) IDENTIFICATION METHOD: by experiment
(D) OTHER INFORMATION: /label= Xaa at location 1
/note= Na-9-fluorenylmethyloxycarbonylglycine
(A) NAME/KEY: Modified-site
(B) LOCATION: 2
(C) IDENTIFICATION METHOD: by experiment
(D) OTHER INFORMATION: /label= Xaa at location 2
/note= Ng-trityl-L-asparagine
(A) NAME/KEY: Modified-site
(B) LOCATION: 4
(C) IDENTIFICATION METHOD: by experiment
(D) OTHER INFORMATION: /label= Xaa at location 4
/note= Nim-trityl-L-histidine
(A) NAME/KEY: Modified-site
(B) LOCATION: 6
(C) IDENTIFICATION METHOD: by experiment
(D) OTHER INFORMATION: /label= Xaa at location 6
/note= O-t-butyl-L-threonine
(A) NAME/KEY: Modified-site
(B) LOCATION: 9
(C) IDENTIFICATION METHOD: by experiment (D) OTHER INFORMATION: /label= Xaa at location 9
/note= L-aspartic acid b-t-butyl ester (xi) SEQUENCE DESCRIPTION: SEQ ID NO:19:

```
Xaa Xaa Trp Xaa Gly Xaa Ala Pro Xaa
1               5
```

(2) INFORMATION FOR SEQ ID NO:20:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 2
(C) IDENTIFICATION METHOD: by experiment
(D) OTHER INFORMATION: /label= Xaa at location 2
/note= Ng-trityl-L-asparagine
(A) NAME/KEY: Modified-site
(B) LOCATION: 4
(C) IDENTIFICATION METHOD: by experiment
(D) OTHER INFORMATION: /label= Xaa at location 4
/note= Nim-trityl-L-histidine
(A) NAME/KEY: Modified-site
(B) LOCATION: 6
(C) IDENTIFICATION METHOD: by experiment
(D) OTHER INFORMATION: /label= Xaa at location 6
/note= O-t-butyl-L-threonine
(A) NAME/KEY: Modified-site
(B) LOCATION: 9
(C) IDENTIFICATION METHOD: by experiment
(D) OTHER INFORMATION: /label= Xaa at location 9
/note= L-aspartic acid a-p-nitrobenzyl ester (xi) SEQUENCE DESCRIPTION: SEQ ID NO:20:

```
Gly Xaa Trp Xaa Gly Xaa Ala Pro Xaa
1               5
```

(2) INFORMATION FOR SEQ ID NO:21:

(i) SEQUENCE CHARACTERISTICS:
(A) LENGTH: 24 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 24
(C) IDENTIFICATION METHOD: by experiment
(D) OTHER INFORMATION: /label= Xaa at location 24
/note= L-prolinamide (xi) SEQUENCE DESCRIPTION: SEQ ID NO:21:

```
Leu Gly Lys Leu Ser Gln Glu Leu His Lys Leu Gln Thr Tyr Pro
1               5                   10                  15

Arg Thr Asn Thr Gly Ser Gly Thr Xaa
                20
```

(2) INFORMATION FOR SEQ ID NO:22:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 25
(C) IDENTIFICATION METHOD: by experiment
(D) OTHER INFORMATION: /label= Xaa at location 25
/note= L-prolinamide (xi) SEQUENCE DESCRIPTION: SEQ ID NO:22:

```
Val Leu Gly Lys Leu Ser Gln Glu Leu His Lys Leu Gln Thr Tyr
1               5                   10                  15

Pro Arg Thr Asn Thr Gly Ser Gly Thr Xaa
                20                  25
```

(2) INFORMATION FOR SEQ ID NO:23:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 25
(C) IDENTIFICATION METHOD: by experiment
(D) OTHER INFORMATION: /label= Xaa at location 25
/note= L-prolinamide (xi) SEQUENCE DESCRIPTION: SEQ ID NO:23:

```
Val Leu Ala Ala Leu Ala Ala Ala Leu Ala Ala Leu Ala Ala Leu
1               5                   10                  15

Pro Arg Thr Asn Thr Gly Ser Gly Thr Xaa
                20                  25
```

(2) INFORMATION FOR SEQ ID NO:24:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 25
(C) IDENTIFICATION METHOD: by experiment
(D) OTHER INFORMATION: /label= Xaa at location 25
/note= L-prolinamide (xi) SEQUENCE DESCRIPTION: SEQ ID NO:24:

```
Met Leu Gly Thr Tyr Thr Gln Asp Phe Asn Lys Phe His Thr Phe
1               5                   10                  15

Pro Gln Thr Ala Ile Gly Val Gly Ala Xaa
                20                  25
```

(2) INFORMATION FOR SEQ ID NO:25:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 25
(C) IDENTIFICATION METHOD: by experiment
(D) OTHER INFORMATION: /label= Xaa at location 25
/note= L-prolinamide (xi) SEQUENCE DESCRIPTION: SEQ ID NO:25:

```
Gly Leu Gly Ser Leu Thr Glu Val Leu Ala Lys Leu Ala Ala Tyr
1               5                   10                  15

Pro Arg Thr Asn Thr Gly Ser Gly Thr Xaa
                20                  25
```

(2) INFORMATION FOR SEQ ID NO:26:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 25
(C) IDENTIFICATION METHOD: by experiment
(D) OTHER INFORMATION: /label= Xaa at location 25
/note= L-prolinamide (xi) SEQUENCE DESCRIPTION: SEQ ID NO:26:

```
Gly Leu Gly Ser Leu Thr Glu Val Leu Ala Lys Leu Ala Ala Tyr
1               5                   10                  15

Pro Arg Ser Gln Thr Gly Ala Gly Thr Xaa
                20                  25
```

(2) INFORMATION FOR SEQ ID NO:27:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 16
(C) IDENTIFICATION METHOD: by experiment
(D) OTHER INFORMATION: /label= Xaa at location 16
/note= trans-4-hydroxy-L-proline
(A) NAME/KEY: Modified-site
(B) LOCATION: 25
(C) IDENTIFICATION METHOD: by experiment
(D) OTHER INFORMATION: /label= Xaa at location 25
/note= trans-4-hydroxy-L-prolinamide (xi) SEQUENCE DESCRIPTION: SEQ ID NO:27:

```
Gly Leu Gly Ser Leu Thr Glu Val Leu Ala Lys Leu Ala Ala Tyr
1               5                   10                  15

Xaa Arg Thr Asn Thr Gly Ser Gly Thr Xaa
                20                  25
```

(2) INFORMATION FOR SEQ ID NO:28:

(i) SEQUENCE CHARACTERISTICS:
(A) LENGTH: 25 amino acids
(B) TYPE: amino acid
(C) STRANDEDNESS: single

```
        (D) TOPOLOGY: linear

   (ii) MOLECULE TYPE: peptide

   (ix) FEATURE:
        (A) NAME/KEY: Modified-site
        (B) LOCATION: 21
        (C) IDENTIFICATION METHOD: by experiment
        (D) OTHER INFORMATION: /label= Xaa at location 21
             /note=  b-alanine
        (A) NAME/KEY: Modified-site
        (B) LOCATION: 25
        (C) IDENTIFICATION METHOD: by experiment
        (D) OTHER INFORMATION: /label= Xaa at location 25
             /note=  L-prolinamide

     (xi) SEQUENCE DESCRIPTION: SEQ ID NO:28:

Gly Leu Gly Ser Leu Thr Glu Val Leu Ala Lys Leu Ala Ala Tyr
1               5                   10                  15

Pro Arg Thr Asn Thr Xaa Ser Gly Thr Xaa
                20                  25


(2) INFORMATION FOR SEQ ID NO:29:

    (i) SEQUENCE CHARACTERISTICS:
        (A) LENGTH: 25 amino acids
        (B) TYPE: amino acid
        (C) STRANDEDNESS: single
        (D) TOPOLOGY: linear

   (ii) MOLECULE TYPE: peptide

   (ix) FEATURE:
        (A) NAME/KEY: Modified-site
        (B) LOCATION: 25
        (C) IDENTIFICATION METHOD: by experiment
        (D) OTHER INFORMATION: /label= Xaa at location 25
             /note=  trans-4-hydroxy-L-prolinamide

     (xi) SEQUENCE DESCRIPTION: SEQ ID NO:29:

Gly Leu Gly Ser Leu Thr Glu Val Leu Ala Lys Leu Ala Glu Tyr
1               5                   10                  15

Pro Arg Thr Asn Thr Gly Ser Gly Thr Xaa
                20                  25


(2) INFORMATION FOR SEQ ID NO:30:

    (i) SEQUENCE CHARACTERISTICS:
        (A) LENGTH: 25 amino acids
        (B) TYPE: amino acid
        (C) STRANDEDNESS: single
        (D) TOPOLOGY: linear

   (ii) MOLECULE TYPE: peptide

   (ix) FEATURE:
        (A) NAME/KEY: Modified-site
        (B) LOCATION: 7
        (C) IDENTIFICATION METHOD: by experiment
        (D) OTHER INFORMATION: /label= Xaa at location 7
             /note=  g-carboxy-L-glutamic acid
        (A) NAME/KEY: Modified-site
        (B) LOCATION: 25
        (C) IDENTIFICATION METHOD: by experiment
        (D) OTHER INFORMATION: /label= Xaa at location 25
             /note=  L-prolinamide

     (xi) SEQUENCE DESCRIPTION: SEQ ID NO:30:

Gly Leu Gly Ser Leu Thr Xaa Val Leu Ala Lys Leu Ala Glu Tyr
1               5                   10                  15

Pro Arg Thr Asn Thr Gly Ser Gly Thr Xaa
                20                  25
```

-continued (2) INFORMATION FOR SEQ ID NO:31:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 14
(C) IDENTIFICATION METHOD: by experiment
(D) OTHER INFORMATION: /label= Xaa at location 14
/note= g-carboxy-L-glutamic acid
(A) NAME/KEY: Modified-site
(B) LOCATION: 25
(C) IDENTIFICATION METHOD: by experiment
(D) OTHER INFORMATION: /label= Xaa at location 25
/note= L-prolinamide (xi) SEQUENCE DESCRIPTION: SEQ ID NO:31:

```
Gly Leu Gly Ser Leu Thr Glu Val Leu Ala Lys Leu Ala Xaa Tyr
1               5                   10                  15

Pro Arg Thr Asn Thr Gly Ser Gly Thr Xaa
                20                  25
```

(2) INFORMATION FOR SEQ ID NO:32:

(i) SEQUENCE CHARACTERISTICS:
(A) LENGTH: 28 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 26
(C) IDENTIFICATION METHOD: by experiment
(D) OTHER INFORMATION: /label= Xaa at location 26
/note= b-alanine
(A) NAME/KEY: Modified-site
(B) LOCATION: 27, 28
(C) IDENTIFICATION METHOD: by experiment
(D) OTHER INFORMATION: /label= Xaa at location 27
/note= is Lys crosslinked to Xaa which is Pro
at location 28

(xi) SEQUENCE DESCRIPTION: SEQ ID NO:32:

```
Gly Leu Gly Ser Leu Thr Glu Val Leu Ala Lys Leu Ala Glu Tyr
1               5                   10                  15

Pro Arg Thr Asn Thr Gly Ser Gly Thr Pro Xaa Xaa Xaa
                20                  25
```

(2) INFORMATION FOR SEQ ID NO:33:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 25
(C) IDENTIFICATION METHOD: by experiment
(D) OTHER INFORMATION: /label= Xaa at location 25

-continued

/note= trans-4-hydroxy-L-prolinamide (xi) SEQUENCE DESCRIPTION: SEQ ID NO:33:

```
Gly Leu Gly Ser Leu Thr Glu Val Leu Ala Lys Leu Ala Glu Tyr
1               5                   10                  15

Xaa Arg Thr Asn Thr Gly Ser Gly Thr Xaa
                20                  25
```

(2) INFORMATION FOR SEQ ID NO:34:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:34:

```
Gly Leu Gly Ser Leu Thr Glu Val Leu Ala Lys Leu Ala Glu Tyr
1               5                   10                  15

Pro Lys Thr Asn Thr Gly Ser Gly Thr Pro
                20                  25
```

(2) INFORMATION FOR SEQ ID NO:35:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:35:

```
Xaa Trp Xaa Gly Thr Ala Xaa
1               5
```

(2) INFORMATION FOR SEQ ID NO:36:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:36:

```
Ser Ala Ala Val Tyr Phe
1               5
```

(2) INFORMATION FOR SEQ ID NO:37:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:37:

```
Phe Ile Gly Trp Gly Asn
1           5
```

(2) INFORMATION FOR SEQ ID NO:38:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:38:

```
Tyr Pro Trp Trp Asn Tyr Arg
1               5
```

(2) INFORMATION FOR SEQ ID NO:39:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:39:

```
Leu Gly Val Gly Lys Ser Xaa Asn
1               5
```

(2) INFORMATION FOR SEQ ID NO:40:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:40:

```
Cys Gly Asn Leu Ser Thr Cys
1               5
```

(2) INFORMATION FOR SEQ ID NO:41:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:41:

```
Ser Gly Asn Leu Ser Thr Ser
1               5
```

(2) INFORMATION FOR SEQ ID NO:42:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:42:

```
Cys Ser Asn Leu Ser Thr Cys
1               5
```

(2) INFORMATION FOR SEQ ID NO:43:

-continued

```
(i) SEQUENCE CHARACTERISTICS:
     (A) LENGTH: 7 amino acids
     (B) TYPE: amino acid
     (C) STRANDEDNESS: single
     (D) TOPOLOGY: linear

(ii) MOLECULE TYPE: peptide

    (xi) SEQUENCE DESCRIPTION: SEQ ID NO:43:

  Ser Ser Asn Leu Ser Thr Ser
  1               5
```

CALCITONIN DERIVATIVES

This application is a Continuation application of application Ser. No. 08/737,570, filed Nov. 15, 1996. now abandoned which is a 371 of PCT/JP96/00666, filed Mar. 15, 1996.

TECHNICAL FIELD

The present invention relates to calcitonin derivatives that have a biological activity, in which a cyclic peptide having a particular structure is bonded to calcitonin, a partial calcitonin peptide or an analogue thereof having an amino acid sequence necessary for the expression of a calcitonin-like biological activity optionally via a spacer.

The peptides of the present invention have higher activity and/or stability than calcitonin, partial calcitonin peptides, or analogues thereof.

BACKGROUND ART

So far, calcitonin, derived from eel, salmon, human beings, pigs, fowl, cattle, sheep, rats and stingray, has been known as natural calcitonin. Calcitonin peptides of such various origins are all polypeptides consisting of 32 amino acids that have the common characteristics, that is, the first and the seventh amino acids are L-cysteine, mercapto groups of these two amino acids form a disulfide bond and the carboxyl terminals are prolinamide.

The disulfide bond of these various calcitonins is expected to be unstable in a solution. To solve this problem, calcitonin derivatives were known to be prepared in which the first amino acid cysteine was deleted, the seventh amino acid cysteine was replaced by α-amino acid having a kind of lower carboxyalkylene group, and the side-chain carboxyl group of this amino acid and α-amino group of the second amino acid were combined to form an amide bond (Japanese Published Unexamined Patent Application Nos. 128993/76, 59688/78, and 112099/86). Particularly, the analogues based on the eel calcitonin sequence have been provided for practicable use as therapeutic agents against bone Paget disease, hypercalcemia, and osteoporosis. Analogues of this type in which single bonds in alkylene chain are partially replaced by double bond(s) or triple bond(s) are also known (WO 93/15106). As calcitonin analogues prepared for the same purpose, there are also known polypeptides in which the first amino acid is replaced by glycine or β-alanine, the seventh amino acid is replaced by aspartic acid or glutamic acid, and an amide bond is formed between the α-amino group of the former and the side-chain carboxyl group of the latter, and peptides in which alkylene groups are partially replaced by phenylene group in addition to the above modifications (Japanese Published Unexamined Patent Application Nos. 262595/90 and 178993/91).

Further, many kinds of calcitonin analogues prepared for the purpose of improving physiological activities of natural calcitonin have been reported [e.g., Endocrinology, vol. 117, p. 801 (1985), Eur. J. Biochem., vol. 159, p. 125 (1986), Biochem. Biophys, Res. Commun., vol. 152, p. 203 (1988), Endocrinology, vol. 127, p. 163 (1990)].

DISCLOSURE OF THE INVENTION

The present invention relates to compounds represented by formula (I):

$$\overline{\underline{|}\,Z-(X)_m-\underline{|}}\!Asp-(Trp)_n-Y \qquad (I)$$

wherein Z represents Gly or Cys; X represents an α-amino acid residue; Y represents a natural calcitonin moiety, a partial natural calcitonin peptide moiety, or a natural calcitonin-like peptide moiety; m represents an integer of 5–8 α-amino acid residues represented by X being the same or different; and n represents an integer of 0–3; provided that when m is 5, the sequence of 4 C-terminal residues of $-(X)_m-$ is different from the sequence of the third to sixth amino acids of natural calcitonin, and pharmaceutically acceptable salts thereof.

Hereinafter, peptide compounds represented by formula (I) are referred to as Compounds (I).

In the definition of formula (I), the α-amino acid residue means a residue of natural amino acids such as glycine, L- or D-alanine, asparagine, aspartic acid, arginine, cysteine, glutamine, glutamic acid, histidine, isoleucine, leucine, lysine, methionine, phenylalanine, proline, serine, threonine, tryptophan, tyrosine, and valine, or a residue of non-natural amino acids such as β-alanine, γ-aminobutyric acid, aminobenzoic acid, L- or D-hydroxyproline, norvaline, and β-2-naphthylalanine.

Examples of $-(X)_m-$ in formula (I) are -$X^1$-Trp-$X^2$-Gly-Thr-Ala-$X^3$-(SEQ ID NO: 35) (wherein $X^1$ represents Asn or Asp; $X^2$ represents His or Lys; and $X^3$ represents Pro or Ala), -Ser-Ala-Ala-Val-Tyr-Phe-(SEQ ID NO: 36), -Phe-Ile-Gly-Trp-Gly-Asn-(SEQ ID NO: 37), -Tyr-Pro-Trp-Trp-Asn-Tyr-Arg-(SEQ ID NO: 38), and -Leu-Gly-Val-Gly-Ser-$X^4$-Asn-(SEQ ID NO: 39) (wherein $X^4$ represents Cys, Ala or Ser).

The natural calcitonin moiety represented by Y means a peptide moiety having a natural calcitonin-like physiological activity. The partial natural calcitonin peptide moiety or natural calcitonin-like peptide moiety represented by Y means a peptide moiety whose amino acid sequence has at least more than 20% homology to at least one amino acid sequence of natural calcitonin moiety, and the moiety represented by the following formula (II) may be given as an example:

$$P^1-P^2-Leu-P^3-P^4-P^5-P^6-P^7-P^6-P^8-P^9-P^{10}-P^{11}-P^{12}$$
$$P^{13}-P^{14}-P^{15}-P^{16}-P^{17}-Gly-P^{18}-P^{11}-P^{19} \qquad (II)$$

wherein $P^1$ represents a single bond, Cys-Gly-Asn-Leu-Ser-Thr-Cys (SEQ ID NO: 40), Ser-Gly-Asn-Leu-Ser-Thr-Ser (SEQ ID NO: 41), Cys-Ser-Asn-Leu-Ser-Thr-Cys (SEQ ID NO: 42) or Ser-Ser-Asn-Leu-Ser-Thr-Ser (SEQ ID NO: 43); $P^2$ represents Val, Met, Gly or a single bond; $P^3$ represents Gly-Lys, Ala-Ala, Gly-Thr or Gly-Ser; $P^4$ represents Leu or Tyr; $P^5$ represents Ser-Gln-Glu, Ala-Ala-Ala, Thr-Gln-Asp, Thr-Glu-Val or Thr-Gla-Val; $P^6$ represents Leu or Phe; $P^7$ represents His-Lys, Ala-Ala, Asn-Lys or Ala-Lys; $P^8$ represents Gln, Ala or His; $P^9$ represents Thr, Ala, Glu or Gla; $P^{10}$ represents Tyr, Phe or Leu; $P^{11}$ represents Pro or Hyp; $P^{12}$ represents Arg, Gln, Lys or D-Arg; $P^{13}$ represents Thr or Ser; $P^{14}$ represents Asn, Gln or Ala; $P^{15}$ represents Thr or Ile; $P^{16}$ represents Gly or β-Ala; $P^{17}$ represents Ser, Val or Ala; $P^{18}$ represents Thr or Ala; and $P^{19}$ represents amino group or a group represented by the following formula (III). In the amino acid sequence represented by formula (II), at least one amino acid may be deleted, inserted or substituted.

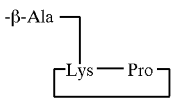

(III)

The pharmaceutically acceptable salts of Compounds (I) include acid addition salts, metal salts, and organic base addition salts. Examples of the pharmaceutically acceptable acid addition salts are inorganic acid addition salts such as hydrochloride, sulfate, and phosphate, and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminum salt, and zinc salt. Examples of the pharmaceutically acceptable organic base addition salts are salts with primary amines such as methylamine, ethylamine, and aniline, secondary amines such as dimethylamine, diethylamine, pyrrolidine, piperidine, morpholine, and piperazine, and tertiary amines such as trimethylamine, triethylamine, N,N-dimethylaniline, and pyridine, and ammonium salts.

The present invention is described in detail below.

The abbreviations for amino acids and their protecting groups used herein follow the recommendations by IUPAC-IUB Joint Commission on Biochemical Nomenclature [Eur. J. Biochem., vol. 138, p. 9 (1984)].

The abbreviations for amino acids and their protecting groups are as follows, unless otherwise specified.

Gly; Glycine
Ala; L-Alanine
β-Ala; β-Alanine
Thr; L-Threonine
Pro; L-Proline
Hyp; Trans-4-hydroxy-L-proline
Asp; L-Aspartic acid
Asn; L-Asparagine
Asx; L-Aspartic acid or L-asparagine
Glu; L-Glutamic acid
Gln; L-Glutamine
Gla; γ-Carboxy-L-glutamic acid
Glx; L-Glutamic acid, L-glutamine or γ-carboxy-L-glutamic acid
His; L-Histidine
Trp; L-Tryptophan
Val; L-Valine
Leu; L-Leucine
Ser; L-Serine
Met; L-Methionine
Cys; L-Cysteine
Ile; L-Isoleucine
Phe; L-Phenylalanine
Tyr; L-Tyrosine
Lys; L-Lysine
Arg; L-Arginine
D-Arg; D-Arginine
Fmoc; 9-Fluorenylmethyloxycarbonyl
t-Bu; t-Butyl
Trt; Trityl
Bzl; Benzyl
$Bzl(NO_2)$; p-Nitrobenzyl
Pmc; 2,2,5,7,8-Pentamethylchroman-6-sulfonyl
Boc; t-Butyloxycarbonyl The abbreviations for side-chain-protected amino acids are as follows.

Fmoc-Asp-OBzl $(NO_2)$; $N^{\alpha}$-9-Fluorenylmethyloxycarbonyl-L-aspartic acid p-nitrobenzyl ester
Fmoc-Asp (Ot-Bu)-OBzl $(NO_2)$; β-t-Butyl α-p-nitrobenzyl $N^{\alpha}$-9-fluorenylmethyloxycarbonyl-L-aspartate
Fmoc-Asp(Ot-Bu)-OH; $N^{\alpha}$-9-Fluorenylmethyloxycarbonyl-L-aspartic acid β-t-butyl ester
Fmoc-Glu(Ot-Bu)-OH; $N^{\alpha}$-9-Fluorenylmethyloxycarbonyl-L-glutamic acid γ-t-butyl ester
Fmoc-Gla$(Ot-Bu)_2$-OH; y,y-Di-t-butyl $N^{\alpha}$-9-fluorenylmethyloxycarbonyl-γ-carboxy-L-glutamate
Fmoc-His(Trt)-OH; $N^{\alpha}$-9-Fluorenylmethyloxycarbonyl-$N^{im}$-trityl-L-histidine
Fmoc-Thr(t-Bu)-OH; $N^{\alpha}$-9-Fluorenylmethyloxycarbonyl-Oβ-t-butyl-L-threonine
Fmoc-Ser(t-Bu)-OH; $N^{\alpha}$-9-Fluorenylmethyloxycarbonyl-O-t-butyl-L-serine
Fmoc-Tyr(t-Bu)-OH; $N^{\alpha}$-9-Fluorenylmethyloxycarbonyl-O-t-butyl-L-tyrosine
Fmoc-Hyp(t-Bu)-OH; $N^{\alpha}$-9-Fluorenylmethyloxycarbonyl-O-t-butyl-trans-4-hydroxy-L-proline
Fmoc-Lys(Boc)-OH; $N^{\alpha}$-9-Fluorenylmethyloxycarbonyl-$N^{\epsilon}$-t -butyloxycarbonyl-L-lysine
Fmoc-Asn(Trt)-OH; $N^{\alpha}$-9-Fluorenylmethyloxycarbonyl-$N^{\gamma}$-trityl-L-asparagine
Fmoc-Gln(Trt)-OH; $N^{\alpha}$-9-Fluorenylmethyloxycarbonyl-$N^{\delta}$-trityl-L-glutamine
Fmoc-Arg(Pmc)-OH; $N^{\alpha}$-9-Fluorenylmethyloxycarbonyl-$N^{g}$-2,2,5,7,8-pentamethylchroman-6-sulfonyl-L-arginine
H-Trp-OBzl; L-Tryptophanbenzylester The abbreviations for reaction solvents, reaction reagents, etc. are as follows.

PyBOP; Benzotriazol-1-yloxytrispyrrolidinophosphonium hexafluorophosphate
HOBt; N-Hydroxybenzotriazole
NMM; N-Methylmorpholine
DMF; N,N-Dimethylformamide
DCM; Dichloromethane
TFA; Trifluoroacetic acid
DIEA; Diisopropylethylamine
Pd/C; Palladium on carbon catalyst
αMEM; Minimum medium
FCS; Fetal calf serum
BSA; Bovine serum albumin
HEPES; N-2-Hydroxyethylpiperazine-N'-2-ethansulfonic acid
PBS; Phosphate-buffered saline
TRAP; Tartaric acid-resistant acidic phosphatase The process for producing Compounds (I) is described below.

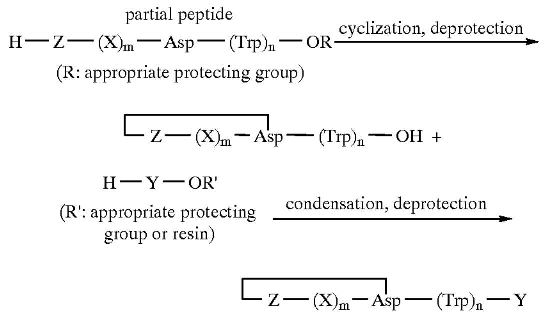

In the above formulae, Z, X, Y, m and n have the same significances as defined above.

The cyclic peptide moiety of Compound (I) can be obtained by synthesizing a partial peptide with appropriately protected side chain by the use of a peptide synthesizer described below or according to a conventional liquid-phase peptide synthetic method (Fundamentals and Experiments of Peptide Synthesis, Nobuo Izumiya et al., Maruzen), and subjecting the resulting product to cyclization using a condensing agent such as PyBOP.

Compound (I) can be obtained by condensing the above cyclic peptide and a C-terminal straight chain peptide which is obtained by the use of a peptide synthesizer and/or according to a liquid-phase peptide synthetic method.

The synthesis of a peptide by the use of a peptide synthesizer is carried out with commercially available peptide synthesizers from Shimadzu Corporaten, Applied Biosystems, Inc., U.S.A. (ABI), etc. using an appropriately side-chain-protected $N^{\alpha}$-9-fluorenylmethyloxycarbonyl amino acid according to respective synthesis programs.

Protected amino acids which are starting materials for the synthesis of Compound (I) and carrier resins are available from ABI, Shimadzu Corporation, Kokusan Chemical Works Co., Ltd., Nova Biochem Co., Watanabe Chemical Co., Ltd. and Peptide Institute Co., Ltd.

Compound (I) thus obtained can be purified by high performance liquid chromatography (hereinafter referred to as HPLC) using C-4, C-8, or C-18 reversed-phase silica gel column, partition, column chromatography using adsorption resins, silica gel, chemically-modified silica gel, reversed-phase silica gel, alumina, diatomaceous earth, magnesium silicate, or ion-exchange resins, gel filtration column chromatography, or thin layer chromatography.

The pharmaceutically acceptable salts of Compound (I) are obtained according to an ordinary method. That is, the acid addition salts and organic base addition salts of Compound (I) are obtained by dissolving Compound (I) in an aqueous solution of the corresponding acid or organic base, followed by freeze-drying. The metal salts of Compound (I) are obtained by dissolving Compound (I) in an aqueous solution containing the corresponding metal ions, followed by purification by gel filtration or HPLC.

Specific examples of Compounds (I) are shown in Table 1.

TABLE 1

| Compound No. | Sequence | |
|---|---|---|
| Compound 1 | GNWHGTAPDWLGKLSQELHKLQTYPRTNTGSGTP—$NH_2$ | (SEQ ID NO:1) |
| Compound 2 | GNWHGTAPDVLGKLSQELHKLQTYPRTNTGSGTP—$NH_2$ | (SEQ ID NO:2) |
| Compound 3 | GNWHGTAPDVLAALAAALAALAALPRTNTGSGTP—$NH_2$ | (SEQ ID NO:3) |
| Compound 4 | GNWHGTAPDMLGTYTQDFNKFHTFPQTAIGVGAP—$NH_2$ | (SEQ ID NO:4) |
| Compound 5 | GNWHGTAPDGLGSLTEVLAKLAAYPRTNTGSGTP—$NH_2$ | (SEQ ID NO:5) |
| Compound 6 | GNWHGTAPDGLGSLTEVLAKLAAYPRSQTGAGTP—$NH_2$ | (SEQ ID NO:6) |

TABLE 1-continued

| Compound No. | Sequence | |
|---|---|---|
| Compound 7 | GNWHGTAPDGLGSLTEVLAKLAAYHypRTNTGSGTHyp— $NH_2$ | (SEQ ID NO:7) |
| Compound 8 | GNWHGTAPDGLGSLTEVLAKLAAYPRTNTβ-AlaSGTP— $NH_2$ | (SEQ ID NO:8) |
| Compound 9 | GNWHGTAPDGLGSLTEVLAKLAEYPRTNTGSGTP— $NH_2$ | (SEQ ID NO:9) |
| Compound 10 | GNWHGTAPDGLGSLTGlaVLAKLAEYPRTNTGSGTP— $NH_2$ | (SEQ ID NO:10) |
| Compound 11 | GNWHGTAPDGLGSLTEVLAKLAGlaYPRTNTGSGTP— $NH_2$ | (SEQ ID NO:11) |
| Compound 12 | GNWHGTAPDGLGSLTEVLAKLAEYPRTNTGSGTPβ-AlaX | (SEQ ID NO:12) |
| Compound 13 | GNWHGTAPDGLGSLTEVLAKLAEYPrTNTGSGTP— $NH_2$ | (SEQ ID NO:13) |
| Compound 14 | GNWHGTAPDGLGSLTEVLAKLAEYPKTNTGSGTP— $NH_2$ | (SEQ ID NO:14) |

G; Gly, A; Ala, N; Asn, Q; Gln, K; Lys, R; Arg, D; Asp, E; Glu, T; Thr, S; Ser, L; Leu, I; Ile, V; Val, H; His, M; Met, P; Pro, F; Phe, Y; Tyr, W; Trp, r; D-Arg,

X; Lys-Pro

The biological activity and the stability to protease of Compounds 1–14 are described in the following test examples.

TEST EXAMPLE 1

Calcitonin-Like Biological Activity 1-1 Preparation of Osteoclasts

Osteoclast-like multinucleated cells which were derived by coculturing mouse osteoblasts and bone marrow cells on collagen gel according to the method described in Akatsu T. et al., J. Bone Miner. Res., 7, 1297–1306 (1992) were used as osteoclasts. That is, osteoblasts derived from mouse vault of skull ($5\times10^5$ cells) were put in a 100 mm dish (IWAKI) collagen-coated with Cellmatrix Type I-A (Nitta Gelatin Co., Ltd.) and cultured for one day in a $CO_2$ incubator (37° C., 5% $CO_2$) [medium: αMEM+10% FCS (both by GIBCO Co., Ltd.)]. After the medium was removed, mouse bone marrow cells ($6\times10^6$ cells) were put on the osteoblasts and $10^{-8}$ M calcitriol (Wako Pure Chemical Industries, Ltd.) and $10^{-7}$ M dexamethasone (Sigma Chemical Co.) were added thereto. TRAP-positive multinucleate cells (osteoclast-like cells) which were obtained 7 days after the inoculation of osteoblasts were used as osteoclasts.

1-2 Culturing of Osteoclasts on Ivory Pieces

After removal of the medium from the dish, and rinsing with PBS(−), a mixture of collagenase and dispase (collagenase: Wako Pure Chemical Industries, Ltd., dispase: Godo Shusei Co., Ltd.) was added thereto to suspend the cells. The cell suspension was put into a tube and centrifuged at 800 rpm for 5 minutes. After removal of the supernatant by suction, the cells were suspended again in αMEM and the suspension was put on ivory pieces (diameter: 4 mm, thickness: 20 μm) in 100 μl portions. The ivory pieces were left to stand in a $CO_2$ incubator for 2 hours to attach the osteoclasts thereto, and then taken out and gently transferred to a 48-well plate (IWAKI) to which a medium containing a test compound had been added in advance to determine the bone resorption activity 48 hours later according to the method described below. The medium containing the test compound was prepared by adding the test compound dissolved in HEPES buffer to the medium described in 1-1 to give the final concentrations shown in Tables 2 and 3.

1-3 Determination of Bone Resorption Activity by Staining of Ivory Pieces and Measurement of Bone Resorption Pit Area The ivory pieces taken out of the medium were put into a tube containing 0.1 N aqueous ammonia and subjected to sonication treatment with a sonicator for 20–30 seconds to remove the osteoclasts. After being washed with distilled water to remove ammonia, the ivory pieces were dipped in a hematoxylin-eosin staining solution to stain resorption pits. The bone resorption pit formation rate was calculated based on microphotographs of stained ivory pieces according to the following equation by the use of an image analyzer.

$$\text{Bone resorption pit formation rate (\%)} = \frac{\text{Bone resorption pit area}}{\text{Total area of ivory piece}} \times 100$$

The bone resorption inhibitory activity of test compounds were calculated according to the following equation.

$$\text{Bone resorption inhibitory activity (\% inhibition)} = \frac{A - B}{A} \times 100$$

A; Bone resorption pit formation rate obtained using no test compound

B; Bone resorption pit formation rate obtained using a test compound

The results are shown in Tables 2 and 3.

TABLE 2

| Compound No. | Compound concentration (M) | Bone resorption inhibitory activity (% inhibition) |
|---|---|---|
| Compound 1 | $10^{-7}$ | 61 |
| Compound 17 | $10^{-7}$ | 0 |
| Compound 2 | $10^{-8}$ | 36 |
| Compound 18 | $10^{-8}$ | 15 |
| Compound 3 | $10^{-6}$ | 65 |
| Compound 19 | $10^{-6}$ | 6 |

TABLE 3

| Compound No. | Compound concentration (M) | Bone resorption inhibitory activity (% inhibition) |
|---|---|---|
| Compound 4 | $10^{-6}$ | 29 |
| Compound 5 | $10^{-6}$ | 35 |
| Compound 6 | $10^{-6}$ | 29 |
| Compound 7 | $10^{-8}$ | 50 |
| Compound 8 | $10^{-6}$ | 39 |
| Compound 9 | $10^{-6}$ | 53 |
| Compound 10 | $10^{-6}$ | 27 |
| Compound 11 | $10^{-7}$ | 42 |
| Compound 12 | $10^{-7}$ | 59 |
| Compound 13 | $10^{-6}$ | 35 |
| Compound 14 | $10^{-6}$ | 40 |

TEST EXAMPLE 2

Stability to Prolylendopeptidase

A test compound was dissolved in a PBS(−) buffer (pH 7.2) containing 0.01% sodium azide and 0.1 mM calcium chloride to give a concentration of 25 μg/ml. To the solution was added prolylendopeptidase (Seikagaku Corporation) in an amount of 1/50 weight of the test compound. The resulting mixture was incubated at 37° C. in a thermostat and sampled at intervals. The samples were analyzed by HPLC using a reversed-phase column (YMC-Pack ODS-AM 150×6 mm I.D.). Elution was carried out with a linear concentration gradient using 0–45% acetonitrile containing 0.1% TFA for 30 minutes, and the absorbance was measured at 220 nm.

From the values obtained at intervals, the residual rate of the test compound was calculated as a relative value based on the height of the peak for the test compound not treated with prolylendopeptidase, which was regarded as 100%.

The results are shown in FIGS. 1 and 2. As shown in FIG. 1, the residual rate of Compound c after 1 hour was 16%, while that of Compound 1 was 32%. As shown in FIG. 2, the residual rate of Compound d was 9%, while that of Compound 2 was 45%.

TEST EXAMPLE 3

Four-weeks-old male SD strain rats (Clea Japan, Inc.) were fasted for 24 hours before the test and were offered in groups each consisting of 8 rats. Each rat of the control group was given 0.5 ml of physiological saline (Otsuka Pharmaceutical Co., Ltd.) containing 1% BSA (Sigma Chemical Co.) by intravenous administration through the tail vein. In the same manner, each rat of Compound 9-administered groups was given 0.5 ml of a solution of Compound 9 in physiological saline containing 1% BSA. Blood was collected from the right femoral artery of a rat 60 minutes after the administration and was centrifuged at 4° C. at 3000 rpm for 15 minutes to obtain a blood serum, and the serum calcium content was determined with calcium C-test WAKO (Wako Pure Chemical Industries, Ltd.).

The results are expressed in terms of value ± standard error, and the difference was judged to be statistically significant at $P < 0.05$ according to the Williams-Wilcoxon test.

The results are shown in Table 4. The serum calcium content of the Compound 9-administered group at a concentration of 100 μg/l was significantly lowered compared with that of the control group.

TABLE 4

| Compound concentration (μg/ml) | N | Serum calcium Content (mg/dl) |
|---|---|---|
| 0 (Control group) | 8 | 10.09 ± 0.07 |
| 1 | 8 | 10.41 ± 0.13 |
| 10 | 8 | 10.20 ± 0.16 |
| 100 | 8 | 7.54 ± 0.29 ** |

**: $P < 0.01$ (comparison with control group)

BEST MODE FOR CARRYING OUT THE INVENTION

Figure 1:
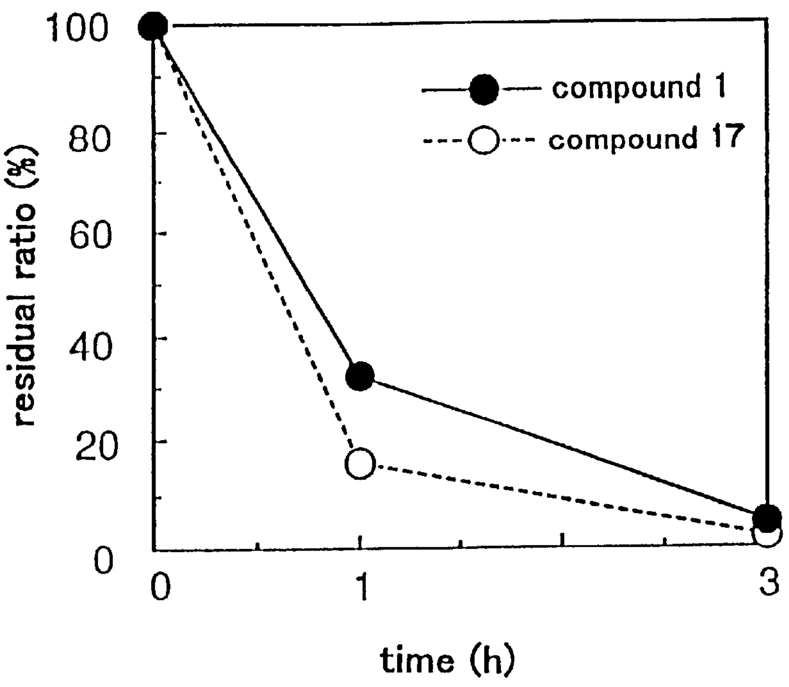
FIG. 1 shows the stability of Compounds 1 and 17 to prolylendopeptidase by the change of the residual rate with the passage of time.
Figure 2:
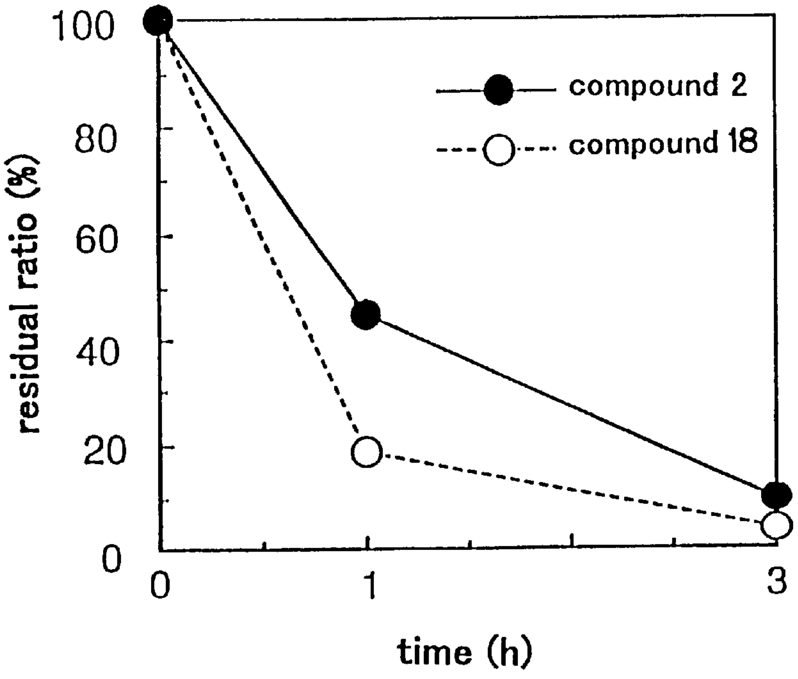
FIG. 2 shows the stability of Compounds 2 and 18 to prolylendopeptidase by the change of the residual rate with the passage of time.

The physicochemical properties of compounds shown in Examples below were determined according to the following methods.

Mass spectrometric analysis was carried out according to the FAB method using JEOL JMS-SX102A.

Amino acid analysis was carried out according to the method by Bidlingmeyer, B. A. et al. [J. Chromatogr., vol. 336, p. 93 (1984)]. Hydrolysis was carried out in hydrochloric acid vapor at 110° C. for 22 hours. The amino acid compositions of the resulting hydrolyzates were analyzed with Waters Pico Tag amino acid analyzer (Waters Associates). The determined values were shown as relative values taking the value for Ala or Leu as the standard value.

EXAMPLE 1

Synthesis of Compound 1

In 1.4 ml of DMF was dissolved 5.0 mg of Compound 15; (SEQ ID NO: 15) obtained in Reference Example 1, and 4.7 mg of PyBOP, 1.2 mg of HOBt and 1.5 μl of NMM were added thereto under ice cooling. The resulting solution was left to stand for 5 minutes under ice cooling and then was added to 53 mg of the carrier resin to which the peptide was bound as obtained in Reference Example 3. The resulting mixture was stirred at 4° C. for 66 hours, followed by further stirring at room temperature for 6 hours. The carrier resin was separated by filtration, washed successively with methanol and butyl ether, and then dried for 1 hour under reduced pressure. To the obtained resin was added 300 μl of a mixture of TFA (82.5%), thioanisole (5%), water (5%), ethyl methyl sulfide (3%), 1,2-ethanedithiol (2.5%), and thiophenol (2%), containing 5 mg/ml 2-methylindole. The resulting mixture was left to stand at room temperature for 6 hours to remove the side-chain-protecting groups and to cleave the peptide from the resin. After the resin was separated by filtration, about 10 ml of ether was added to the filtrate, and the deposited precipitate was collected by centrifugation and decantation to obtain a crude peptide. This peptide was purified by HPLC in the same manner as in Step 2 of Reference Example 1 to give 0.56 mg of Compound 1.

Mass spectrum [FABMS]: 3727 (M+H)

Amino acid analysis: Asx 2.4 (3), Glx 3.1 (3), Ser 2.0 (2), Gly 5.3 (5), His 2.1 (2), Arg 1.1 (1), Thr 5.1 (5), Ala 1.0 (1), Pro 2.8 (3), Tyr 1.0 (1), Leu 4.0 (4), Lys 2.0 (2), Trp was not analyzed.

EXAMPLE 2

Synthesis of Compound 2

In 2.2 ml of DMF was dissolved 11.0 mg of Compound 16; (SEQ ID NO: 16) obtained in Reference Example 2, and 12.0 mg of PyBOP, 3.1 mg of HOBt and 3.8 μl of NMM were added thereto under ice cooling. The resulting solution was left to stand for 5 minutes under ice cooling and then 1.0 ml of the solution was added to 35 mg of the carrier resin to which the peptide was bound as obtained in Reference Example 4. The resulting mixture was stirred at 4° C. for 8 days. The carrier resin was separated by filtration, followed by washing and drying in the same manner as in Example 1. Then the peptide was cleaved from the resin in the same manner as in Example 1 to obtain a crude peptide. This peptide was purified by HPLC in the same manner as in Step 2 of Reference Example 1 to give 0.48 mg of Compound 2. As the reversed-phase column, YMC column (YMC-Pack ODS-AM SH343-5 20 mm I.D.×250 mm) was used.

Mass spectrum [FABMS]: 3640 (M+H)

Amino acid analysis: Asx 2.0 (3), Glx 2.9 (3), Ser 1.9 (2), Gly 5.0 (5), His 1.8 (2), Arg 1.1 (1), Thr 3.9 (5), Ala 1.0 (1), Pro 2.8 (3), Tyr 1.0 (1), Val 0.9 (1), Leu 4.0 (4), Lys 1.6 (2), Trp was not analyzed.

EXAMPLE 3

Synthesis of Compound 3

In 0.92 ml of DMF was dissolved 4.6 mg of Compound 16; (SEQ ID NO: 16) obtained in Reference Example 2, and 7.6 mg of PyBOP, 2.0 mg of HOBt and 2.7 μl of NMM were added thereto under ice cooling. The resulting solution was left to stand for 5 minutes under ice cooling and then 0.46 ml of the solution was added to 24 mg of the carrier resin to which the peptide was bound as obtained in Reference Example 5. The resulting mixture was stirred at 4° C. for 5 days. To the mixture were added 3.8 mg of PyBOP, 1.0 mg of HOBt and 1.4 μl of NMM under ice cooling, followed by stirring at room temperature for 2 days. The carrier resin was separated by filtration, followed by washing and drying in the same manner as in Example 1. Then the peptide was cleaved from the resin in the same manner as in Example 1 to obtain a crude peptide. This peptide was purified by HPLC in the same manner as in Step 2 of Reference Example 1 to give 0.14 mg of Compound 3. As the reversed-phase column, YMC column (YMC-Pack ODS-AM SH343-5 20 mm I.D.×250 mm) was used.

Mass spectrum [FABMS]: 3206 (M+H)

Amino acid analysis: Asx 2.8 (3), Ser 1.2 (1), Gly 4.9 (4), His 1.0 (1), Arg 1.1 (1), Thr 4.4 (4), Ala 9.5 (10), Pro 3.3 (3), Val 0.8 (1), Leu 5.0 (5), Trp was not analyzed.

EXAMPLE 4

Synthesis of Compound 4

In 1.0 ml of DMF was dissolved 3.67 mg of Compound 16; (SEQ ID NO: 16) obtained in Reference Example 2, and 4.07 mg of PyBOP, 1.20 mg of HOBt monohydrate and 1.29 μl of NMM were added thereto under ice cooling. The resulting solution was left to stand for 5 minutes under ice cooling and then was added to 47.2 mg of the carrier resin to which the peptide was bound as obtained in Reference Example 6. The resulting mixture was stirred at 4° C. for 24 hours. The carrier resin was separated by filtration, followed by washing and drying in the same manner as in Example 1. Then the peptide was cleaved from the resin in the same manner as in Example 1 to obtain a crude peptide. This peptide was purified by HPLC in the same manner as in Step 2 of Reference Example 1 to give 6.4 mg of Compound 4.

Mass spectrum [FABMS]: 3656 (M+H)

Amino acid analysis: Asx 3.6 (4), Glx 1.9 (2), Gly 4.9 (5), His 1.7 (2), Thr 4.4 (5), Ala 2.8 (3), Pro 2.8 (3), Tyr 0.9 (1), Val 0.9 (1), Met 1.0 (1), Ile 0.9 (1), Leu 1.0 (1), Phe 2.5 (3), Lys 0.9 (1), Trp was not analyzed.

EXAMPLE 5

Synthesis of Compound 5

In 2.5 ml of DMF was dissolved 5.3 mg of Compound 16; (SEQ ID NO: 16) obtained in Reference Example 2, and 7.8 mg of PyBOP, 2.0 mg of HOBt and 2.8 μl of NMM were added thereto under ice cooling. The resulting solution was left to stand for 30 minutes under ice cooling and then 0.55 ml of the solution was added to 17.3 mg of the carrier resin to which the peptide was bound as obtained in Reference Example 7. The resulting mixture was left to stand at 0° C. for 10 minutes, followed by stirring at room temperature for 24 hours. The carrier resin was separated by filtration, followed by washing and drying in the same manner as in Example 1. Then the peptide was cleaved from the resin in the same manner as in Example 1 to obtain a crude peptide. This peptide was purified by HPLC in the same manner as in Step 2 of Reference Example 1 to give 0.36 mg of Compound 5. As the reversed-phase column, YMC column (YMC-Pack ODS-AM SH343-5 20 mm I.D.×250 mm) was used.

Mass spectrum [FABMS]: 3389 (M+H)

Amino acid analysis: Asx 2.5 (3), Glx 1.0 (1), Ser 2.0 (2), Gly 5.8 (6), His 0.8 (1), Arg 1.0 (1), Thr 4.7 (5), Ala 3.7 (4), Pro 2.8 (3), Tyr 1.0 (1), Val 0.9 (1), Leu 4.0 (1), Lys 0.9 (1), Trp was not analyzed.

EXAMPLE 6

Synthesis of Compound 6

In 1.25 ml of DMF was dissolved 5.3 mg of Compound 16; (SEQ ID NO: 16) obtained in Reference Example 2, and 7.8 mg of PyBOP, 2.0 mg of HOBt and 2.8 μl of NMM were added thereto under ice cooling. The resulting solution was left to stand for 30 minutes under ice cooling and then 0.55 ml of the solution was added to 17.1 mg of the carrier resin to which the peptide was bound as obtained in Reference Example 8. The resulting mixture was left to stand at 0° C. for 10 minutes, followed by stirring at room temperature for 13 hours. The carrier resin was separated by filtration, followed by washing and drying in the same manner as in Example 1. Then the peptide was cleaved from the resin in the same manner as in Example 1 to obtain a crude peptide. This peptide was purified by HPLC in the same manner as in Step 2 of Reference Example 1 to give 0.39 mg of Compound 6. As the reversed-phase column, YMC column (YMC-Pack ODS-AM SH343-5 20 mm I.D.×250 mm) was used.

Mass spectrum [FABMS]: 3373 (M+H)

Amino acid analysis: Asx 1.7 (2), Glx 2.1 (2), Ser 2.1 (2), Gly 6.2 (6), His 0.8 (1), Arg 1.0 (1), Thr 3.7 (4), Ala 4.7 (5), Pro 2.8 (3), Tyr 0.9 (1), Val 0.9 (1), Leu 4.0 (4), Lys 1.0 (1), Trp was not analyzed.

EXAMLPLE 7

Synthesis of Compound 7

In 2.5 ml of DMF was dissolved 5.3 mg of Compound 16; SEQ ID NO: 16) obtained in Reference Example 2, and 7.8 mg of PyBOP, 2.0 mg of HOBt and 2.8 μl of NMM were added thereto under ice cooling. The resulting solution was left to stand for 30 minutes under ice cooling and then 0.55 ml of the solution was added to 18.2 mg of the carrier resin to which the peptide was bound as obtained in Reference Example 9. The resulting mixture was left to stand at 0° C. for 10 minutes, followed by stirring at room temperature for 24 hours. The carrier resin was separated by filtration, followed by washing and drying in the same manner as in Example 1. Then the peptide was cleaved from the resin in the same manner as in Example 1 to obtain a crude peptide. This peptide was purified by HPLC in the same manner as in Step 2 of Reference Example 1 to give 0.45 mg of Compound 7. As the reversed-phase column, YMC column (YMC-Pack ODS-AM SH343-5 20 mm I.D.×250 mm) was used.

Mass spectrum [FABMS]: 3421 (M+H)

Amino acid analysis: Asx 2.5 (3), Glx 1.0 (1), Ser 2.0 (2), Gly 5.9 (6), His 0.8 (1), Arg 1.0 (1), Thr 4.6 (5), Ala 3.7 (4), Pro 0.8 (1), Tyr 0.9 (1), Val 0.9 (1), Leu 4.0 (4), Lys 1.0 (1), Trp and Hyp were not analyzed.

EXAMPLE 8

Synthesis of Compound 8

In 1.25 ml of DMF was dissolved 5.3 mg of Compound 16; (SEQ ID NO: 16) obtained in Reference Example 2, and 7.8 mg of PyBOP, 2.0 mg of HOBt and 2.8 μl of NMM were added thereto under ice cooling. The resulting solution was left to stand for 30 minutes under ice cooling and then 0.7 ml of the solution was added to 18.1 mg of the carrier resin to which the peptide was bound as obtained in Reference Example 10. The resulting mixture was left to stand at 0° C. for 10 minutes, followed by stirring at room temperature for 13 hours. The carrier resin was separated by filtration, followed by washing and drying in the same manner as in Example 1. Then the peptide was cleaved from the resin in the same manner as in Example 1 to obtain a crude peptide. This peptide was purified by HPLC in the same manner as in Step 2 of Reference Example 1 to give 0.67 mg of Compound 8. As the reversed-phase column, YMC column (YMC-Pack ODS-AM SH343-5 20 mm I.D.×250 mm) was used.

Mass spectrum [FABMS]: 3403 (M+H)

Amino acid analysis: Asx 2.6 (3), Glx 1.0 (1), Ser 2.1 (2), Gly 5.1 (5), His +β-Ala 2.0 (2), Arg 1.0 (1), Thr 4.7 (5), Ala 3.7 (4), Pro 2.9 (3), Tyr 0.9 (1), Val 0.9 (1), Leu 4.0 (4), Lys 1.0 (1), Trp was not analyzed. His and β-Ala were determined collectively because they could not be separated from each other.

EXAMPLE 9

Synthesis of Compound 9

In 3.0 ml of DMF was dissolved 8.1 mg of Compound 16; (SEQ ID NO: 16) obtained in Reference Example 2, and 13.2 mg of PyBOP, 3.4 mg of HOBt and 4.65 μl of NMM were added thereto under ice cooling. The resulting solution was left to stand for 30 minutes under ice cooling and then 1.0 ml of the solution was added to 26.8 mg of the carrier resin to which the peptide was bound as obtained in Reference Example 11. The resulting mixture was stirred at 4° C. for 6 days. The carrier resin was separated by filtration, followed by washing and drying in the same manner as in Example 1. Then the peptide was cleaved from the resin in the same manner as in Example 1 to obtain 19.2 mg of a crude peptide. This peptide was purified by HPLC in the same manner as in Step 2 of Reference Example 1 to give 0.58 mg of Compound 9. As the reversed-phase column, YMC column (YMC-Pack ODS-AM SH343-5 20 mm I.D.× 250 mm) was used.

Mass spectrum [FABMS]: 3447 (M+H)

Amino acid analysis: Asx 2.8 (3), Glx 2.6 (2), Ser 2.1 (2), Gly 6.0 (6), His 0.9 (1), Arg 1.2 (1), Thr 4.9 (5), Ala 3.2 (3), Pro 3.0 (3), Tyr 1.0 (1), Val 1.0.(1), Leu 4.0 (4), Lys 1.2 (1), Trp was not analyzed.

EXAMPLE 10

Synthesis of Compound 10

In 3.0 ml of DMF was dissolved 8.1 mg of Compound 16: (SEQ ID NO: 16) obtained in Reference Example 2, and 13.2 mg of PyBOP, 3.4 mg of HOBt and 4.65 μl of NMM were added thereto under ice cooling. The resulting solution was left to stand for 30 minutes under ice cooling and then 1.0 ml of the solution was added to 27.4 mg of the carrier resin to which the peptide was bound as obtained in Reference Example 12. The resulting mixture was stirred at 4° C. for 6 days. The carrier resin was separated by filtration, followed by washing and drying in the same manner as in Example 1. Then the peptide was cleaved from the resin in the same manner as in Example 1 to obtain 19.2 mg of a crude peptide. This peptide was purified by HPLC in the same manner as in Step 2 of Reference Example 1 to give 0.70 mg of Compound 10. As the reversed-phase column, YMC column (YMC-Pack ODS-AM SH343-5 20 mm I.D.×250 mm) was used.

Mass spectrum [FABMS]: 3491 (M+H)

Amino acid analysis: Asx 2.5 (3), Glx 2.2 (2), Ser 2.0 (2), Gly 5.7 (6), His 0.8 (1), Arg 1.0 (1), Thr 4.7 (5), Ala 3.0 (3), Pro 2.9 (3), Tyr 1.0 (1), Val 0.9 (1), Leu 4.0 (4), Lys 1.1 (1), Gla was detected as Glx. Trp was not analyzed.

EXAMPLE 11

Synthesis of Compound 11

In 3.0 ml of DMF was dissolved 8.1 mg of Compound 16: (SEQ ID NO: 16) obtained in Reference Example 2, and 13.2 mg of PyBOP, 3.4 mg of HOBt and 4.65 μl of NMM were added thereto under ice cooling. The resulting solution was left to stand for 30 minutes under ice cooling and then 0.5 ml of the solution was added to 15.6 mg of the carrier resin to which the peptide was bound as obtained in Reference Example 13. The resulting mixture was stirred at 4° C. for 6 days. The carrier resin was separated by filtration, followed by washing and drying in the same manner as in Example 1. Then the peptide was cleaved from the resin in the same manner as in Example 1 to give 10.8 mg of a crude peptide. This peptide was purified by HPLC in the same manner as in Step 2 of Reference Example 1 to give 0.14 mg of Compound 11. As the reversed-phase column, YMC column (YMC-Pack ODS-AM SH343-5 20 mm I.D.×250 mm) was used.

Mass spectrum [FABMS]: 3491 (M+H)

Amino acid analysis: Asx 2.0 (3), Glx 2.2 (2), Ser 1.6 (2), Gly 5.1 (6), His 0.7 (1), Arg 0.8 (1), Thr 3.7 (5), Ala 2.8 (3), Pro 2.2 (3), Tyr 0.9 (1), Val 1.0 (1), Leu 4.0 (4), Lys 1.0 (1), Gla was detected as Glx. Trp was not analyzed.

EXAMPLE 12

Synthesis of Compound 12

In 3.0 ml of DMF was dissolved 8.1 mg of Compound 16; (SEQ ID NO: 16) obtained in Reference Example 2, and 13.2 mg of PyBOP, 3.4 mg of HOBt and 4.65 μl of NMM were added thereto under ice cooling. The resulting solution was left to stand for 30 minutes under ice cooling and then 0.5 ml of the solution was added to two of the pinheads to which the peptide was bound as obtained in Reference Example 14. The resulting mixture was stirred at 4° C. for 6 days. The pinheads were separated by filtration, followed by washing and drying in the same manner as in Example 1. Then the side-chain-protecting groups were removed therefrom in the same manner as in the cleavage of the peptide in Example 1. After discharge of the solution, the pinheads were washed with methanol and dried under reduced pressure to give the pinheads to which the peptide free from side-chain-protecting groups was bound. To these pinheads was added 0.5 ml of 0.05 M HEPES buffer (pH 8.2), and the resulting mixture was left to stand at room temperature for 5 hours to cleave the peptide from the pinheads. Then the resulting solution containing the peptide was purified by HPLC in the same manner as in Step 2 of Reference Example 1 to give 0.06 mg of Compound 12. As the reversed-phase column, YMC column (YMC-Pack ODS-AM SH343-5 20 mm I.D.×250 mm) was used.

Mass spectrum [FABMS]: 3726 (M+H)

Amino acid analysis: Asx 2.4 (3), Glx 2.2 (2), Ser 1.9 (2), Gly 5.7 (6), His+β-Ala 1.8 (2), Arg 1.1 (1), Thr 4.6 (5), Ala 2.9 (3), Pro 3.9 (4), Tyr 1.1 (1), Val 1.0 (1), Leu 4.0 (4), Lys 2.0 (2), Trp was not analyzed. His and β-Ala were determined collectively because they could not be separated from each other.

EXAMPLE 13

Synthesis of Compound 13

In 0.23 ml of DMF was dissolved 2.2 mg of Compound 16; (SEQ ID NO: 16) obtained in Reference Example 2, and 2.45 mg of PyBOP, 0.72 mg of HOBt and 0.78 μl of NMM were added thereto under ice cooling. The resulting solution was added to 20.8 mg of the carrier resin to which the peptide was bound as obtained in Reference Example 15. The resulting mixture was stirred at 4° C. for 2 days. The carrier resin was separated by filtration, followed by washing and drying in the same manner as in Example 1. Then the peptide was cleaved from the resin in the same manner as in Example 1 to obtain 17.9 mg of a crude peptide. This peptide was purified by HPLC in the same manner as in Step 2 of Reference Example 1 to give 0.39 mg of Compound 13.

Mass spectrum [FABMS]: 3447 (M+H)

Amino acid analysis: Asx 2.2 (3), Glx 2.1 (2), Ser 1.9 (2), Gly 5.6 (6), His 0.7 (1), Arg 1.0 (1), Thr 4.8 (5), Ala 2.9 (3), Pro 2.8 (3), Tyr 1.0 (1), Val 1.0 (1), Leu 4.0 (4), Lys 1.1 (1), Trp was not analyzed.

EXAMPLE 14

Synthesis of Compound 14

In 0.23 ml of DMF was dissolved 2.2 mg of Compound 16; (SEQ ID NO: 16) obtained in Reference Example 2, and 2.45 mg of PyBOP, 0.72 mg of HOBt and 0.78 μl of NMM were added thereto under ice cooling. The resulting solution was added to 20.8 mg of the carrier resin to which the peptide was bound as obtained in Reference Example 16. The resulting mixture was stirred at 4° C. for 2 days. The carrier resin was separated by filtration, followed by washing and drying in the same manner as in Example 1. Then the peptide was cleaved from the resin in the same manner as in Example 1 to obtain 26.3 mg of a crude peptide. This peptide was purified by HPLC in the same manner as in Step 2 of Reference Example 1 to give 0.96 mg of Compound 14.

Mass spectrum [FABMS]: 3419 (M+H)

Amino acid analysis: Asx 2.3 (3), Glx 2.2 (2), Ser 2.0 (2), Gly 5.8 (6), His 0.8 (1), Thr 4.8 (5), Ala 3.0 (3), Pro 2.9 (3), Tyr 1.0 (1), Val. 1.0 (1), Leu 4.0 (4), Lys 2.0 (2), Trp was not analyzed.

REFERENCE EXAMPLE 1

Synthesis of Compound 15; (SEQ ID NO: 15)

Gly—Asn—Trp—His—Gly—Thr—Ala—Pro—Asp—Trp—OH (cyclic: Gly linked to Asp)

Step 1: Synthesis of Fmoc-Gly-Asn(Trt)-Trp-His(Trt)-Gly-Thr(t-Bu)-Ala-Pro-Asp(Ot-Bu)-OH; SEQ ID NO: 19

To 60 mg of a carrier resin (2-chlorotrityl chloride resin) containing 84 μmol of chloro group as the amino acid binding site were added a solution of 17.28 mg (42 μmol) of Fmoc-Asp(Ot-Bu)-OH in a mixture of 0.1 ml of DMF and 0.5 ml of DCM, and 6.1 μl of DIEA, followed by stirring at room temperature for 5 minutes. To this mixture were added 12.2 μl of DIEA and 12.2 μl of DCM, followed by stirring at room temperature for 30 minutes. After addition of 48 μl of methanol, the resulting mixture was further stirred at room temperature for 10 minutes. Then the resin was separated by filtration, washed successively with DCM, DMF, isopropanol, methanol and diethyl ether, and dried for 2 hours under reduced pressure to give the carrier resin to which Fmoc-Asp(Ot-Bu) was bound. To this resin was added 1 ml of a DMF/DCM mixture (1:1) containing 5% piperidine, and the mixture was left to stand for 10 minutes. The resulting mixture was put in a reactor of an automatic synthesizer and the following treatments were carried out according to the synthesis program developed by Shimadzu Corporation.

(a) The carrier resin was washed with DMF for 3 minutes and the rinsings were discharged.

(b) To the carrier resin was added a 30% piperidine-DMF solution, and the mixture was stirred for 4 minutes, followed by discharge of said solution. The same treatment was repeated.

(c) The carrier resin was washed with DMF for one minute and the rinsings were discharged. The same treatment was repeated 5 times. The carrier resin combined with Asp(Ot-Bu) without Fmoc group was thus obtained.

(d) DMF (1.18 ml) containing 336 μmol of Fmoc-Pro-OH, 336 μmol of PyBOP, 336 μmol of HOBt and 504 μmol of NMM was stirred for 3 minutes, and the resulting solution was added to the carrier resin. After stirring for 30 minutes, the solution was discharged.

(e) The carrier resin was washed with DMF for one minute. The same treatment was repeated 5 times. Fmoc-Pro-Asp (Ot-Bu) was thus synthesized on the carrier.

Subsequently, the washing and deprotection steps (a)–(c) were carried out, and condensation reaction was conducted using Fmoc-Ala-OH in Step (d), followed by the washing step (e) to synthesize Fmoc-Ala-Pro-Asp(Ot-Bu) on the carrier resin. Then Steps (a)–(e) were repeated, followed by washing with DCM after the final step to obtain the carrier resin to which a protected peptide was bound. In Step (d) in the repeated procedures, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH were used in turn. To the obtained carrier resin was added 0.9 ml of a mixture of acetic acid (10%), trifluoroethanol (10%) and DCM (80%), and the resulting mixture was left to stand at room temperature for one hour to cleave the peptide from the resin. After the resin was removed by filtration, the solvent was evaporated under reduced pressure to give 37.6 mg of the desired peptide.

Step 2: Synthesis of Fmoc-Gly-Asn(Trt)-Trp-His(Trt)-Gly-Thr(t-Bu)-Ala-Pro-Asp(Ot-Bu)-Trp-OBzl; SEQ ID NO: 17

In 3 ml of DMF was dissolved 10 mg of the peptide obtained in Step 1, and 10.4 mg of PyBOP, 2.7 mg of HOBt and 3.0 μl of NMM were added thereto under ice cooling. The resulting solution was left to stand for 5 minutes under ice cooling. To this solution were added 6.6 mg of H-Trp-OBzl monohydrochloride and 2.0 μl of NMM under ice cooling, followed by stirring at 4° C. for 16 hours. After the neutralization with 2M acetic acid, the mixture was subjected to HPLC using a reversed-phase column (column: product of Shiseido Co., Ltd., CAPCELL PAK C18 30 mm I.D.×250 mm) for purification. Elution was carried out with a linear concentration gradient by adding 90% aqueous acetonitrile containing 0.1% TFA to 0.1% aqueous TFA, followed by detection at 220 nm to give a fraction containing the desired peptide. The obtained fraction was freeze-dried to give 24 mg of the desired peptide.

Step 3: Synthesis of H-Gly-Asn-Trp-His-Gly-Thr-Ala-Pro-Asp-Trp-OBzl; SEQ ID NO: 18

To 24 mg of the peptide obtained in Step 2 was added a solution comprising 1800 μl of TFA, 100 μl of 1,2-ethanedithiol, 100 μl of anisole and 10 mg of 2-methylindole, and the mixture was left to stand at room temperature for 2 hours. To the resulting mixture was added ether, and the deposited white precipitate was collected by centrifugation, followed by drying. To the obtained white powder was added 1 ml of a 20% piperidine/DMF solution and the mixture was left to stand at room temperature for 10 minutes. Ether was again added to the resulting mixture and the deposited white precipitate was collected by centrifugation, followed by drying to give 17.8 mg of the desired peptide.

Step 4: Compound 15; (SEQ ID NO: 15)

(a) In 10 ml of DMF was dissolved 17.8 mg of the peptide obtained in Step 3, and 15.1 mg of PyBOP, 3.9 mg of HOBt and 4.4 μl of NMM were added thereto under ice cooling. The resulting solution was stirred at 4° C. for 15 hours. After neutralization with 2M acetic acid, purification was carried out by HPLC in the same manner as in Step 2 to give 5.3 mg of benzyl ester of Compound a.

(b) To 5.3 mg of benzyl ester obtained in Step (a) were added 1 ml of a saturated methanol solution of ammonium formate and about 10 mg of 10% Pd/C, and the mixture was stirred at room temperature for 2 hours. After separation of Pd/C by filtration, the solvent was evaporated from the filtrate under reduced pressure. The residue was dissolved in 2M acetic acid, followed by purification by HPLC in the same manner as in Step 2 to give 4.5 mg of Compound a.

Mass spectrum [FABMS]: 1122 (M+H)

Amino acid analysis: Gly 2.0 (2), Asx 1.7 (2), His 1.0 (1), Thr 1.0 (1), Ala 1.0 (1), Pro 1.0 (1), Trp was not analyzed.

REFERENCE EXAMPLE 2

Synthesis of Compound 16; (SEQ ID NO: 16)

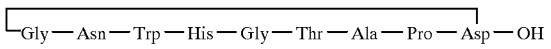

Step 1: Fmoc-Asp-OBzl($NO_2$)

In 25 ml of DMF were suspended 2.06 g of Fmoc-Asp (Ot-Bu)-OH and 0.84 g of sodium hydrogencarbonate, and 5.4 g of p-nitrobenzyl bromide was added thereto, followed by stirring at room temperature for 19 hours. To the reaction mixture were added 200 ml of ethyl acetate and 500 ml of water, and the mixture was shaken. The organic layer was separated and dehydrated over anhydrous sodium sulfate, followed by filtration. To the filtrate was added 60 ml of silica gel (Kieselgel 60, Merck Co., Inc.), and the solvent was evaporated to adsorb the reaction mixture on the gel. The mixture was then applied to a glass column packed with 300 ml of the above-mentioned silica gel and was eluted with a hexane/ethyl acetate mixture as an eluate. A fraction containing Fmoc-Asp(Ot-Bu)-OBzl($NO_2$) was collected, followed by evaporation of the solvent to give 2.24 g of powder. To this powder was added 30 ml of 98% formic acid, and the mixture was allowed to stand at room temperature for 2 hours and then at 37° C. for 2 hours. To the resulting mixture was added 50 ml of 2M acetic acid, followed by freeze-drying to give 1.86 g of the desired compound.

Mass spectrum: 491 (M+H)

Step 2: Synthesis of H-Gly-Asn(Trt)-Trp-His(Trt)-Gly-Thr(t-Bu)-Ala-Pro-Asp-OBzl($NO_2$); SEQ ID NO: 20

To 60 mg of a carrier resin (2-chlorotrityl chloride resin) containing 84 μmol of chloro group as the amino acid binding site were added a solution of 30.9 mg (63 μmol) of Fmoc-Asp-OBzl($NO_2$) obtained in Step 1 in a mixture of 0.1 ml of DMF and 0.5 ml of DCM, and 9.1 μl of DIEA, followed by stirring at room temperature for 5 minutes. To this mixture were added 18.3 μl of DIEA and 18.3 μl of DCM, followed by stirring at room temperature for 30 minutes. After addition of 48 μl of methanol, the resulting mixture was further stirred at room temperature for 10 minutes. Then the resin was separated by filtration, washed successively with DCM, DMF, isopropanol, methanol and diethyl ether, and dried for 2 hours under reduced pressure to give the carrier resin to which Fmoc-Asp-OBzl($NO_2$) was bound via β-carboxylic group of aspartic acid. This resin was used as a starting material for the synthesis in the same manner as in Step 1 of Reference Example 1 according to the synthesis program developed by Shimadzu Corporation using Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH, and Fmoc-Gly-OH in turn. After the treatments of Steps (a)–(c) were carried out, the resin was washed with DCM to obtain the carrier resin to which a side-chain-protected peptide was bound. To this resin was added 0.9 ml of a mixture of acetic acid (10%), trifluoroethanol (10%) and DCM (80%), and the resulting mixture was allowed to stand at room temperature for one hour to cleave the peptide from the resin. After removal of the resin by filtration, the solvent was evaporated under reduced pressure. To the residue was added about 10 ml of ether, and the deposited precipitate was collected by centrifugation and decantation. To the thus obtained powder was added 300 μl of a mixture of TFA (90%), thioanisole (5%) and 1,2-ethanedithiol (5%) containing 5 mg/ml 2-methylindole, and the mixture was left to stand at room temperature for 2 hours. To the resulting mixture was added about 10 ml of ether and the deposited precipitate was collected by centrifugation and decantation to give 139.8 mg of a crude peptide.

Mass spectrum: 1089 [M+H]

Step 3: Compound 16; (SEQ ID NO: 16)

In 10 ml of DMF was dissolved 60 mg of the crude peptide obtained in Step 2, and 57.2 mg of PyBOP, 14.9 mg of HOBt and 18.2 μl of NMM were added thereto under ice cooling, followed by stirring at 4° C. for 22 hours. The reaction mixture was concentrated to 7 ml under reduced pressure, and 7 ml of a 90% aqueous solution of acetic acid was added thereto, followed by ice cooling. To the resulting mixture was added 250 mg of zinc powder and the mixture was left to stand for 10 minutes under ice cooling, followed by stirring at room temperature for one hour. After the reaction mixture was filtered, the filtrate was dried under reduced pressure, and the obtained solid was purified by HPLC in the same manner as in Step 2 of Reference Example 1 to give 15.6 mg of Compound b. As the reversed-phase column, YMC column (YMC-Pack ODS-AM SH343-5 20 mm I.D.×250 mm) was used.

Mass spectrum [FABMS]: 936 (M+H)

REFERENCE EXAMPLE 3

Synthesis of Compound 17 (H-Leu-Gly-Lys-Leu-Ser-Gln-Glu-Leu-His-Lys-Leu-Gln-Thr-Tyr-Pro-Arg-Thr-Asn-Thr-Gly-Ser- Gly-Thr-Pro-$NH_2$; SEQ ID NO: 21)

A carrier resin (Rink amide MBHA resin) (80 mg) to which 40.8 μmol of Fmoc-NH was bound was put in a reactor of an automatic synthesizer and the following treatments were carried out according to the synthesis program developed by Shimadzu Corporation.

(a) The carrier resin was washed with DMF for 3 minutes and the rinsings were discharged.

(b) To the carrier resin was added 900 μl of a 30% piperidine-DMF solution, and the mixture was stirred for 4 minutes, followed by discharge of said solution. The same treatment was repeated.

(c) The carrier resin was washed with DMF for one minute and the rinsings were discharged. The same treatment was repeated 5 times.

The carrier resin combined with NH without Fmoc group was thus obtained.

(d) DMF (1142.4 μl) containing 326.4 μmol of Fmoc-Pro-OH, 326.4 μmol of PyBOP, 326.4 μmol of HOBt monohydrate and 489.6 μmol of NMM was stirred for 3 minutes, and the resulting solution was added to the resin. After stirring for 30 minutes, the solution was discharged.

(e) The carrier resin was washed with DMF for one minute. The same treatment was repeated 5 times. Fmoc-Pro-NH was thus synthesized on the carrier.

Subsequently, the washing and deprotection steps (a)–(c) were carried out, and condensation reaction was conducted using Fmoc-Thr(t-Bu)-OH in Step (d), followed by the washing step (e) to synthesize Fmoc-Thr(t-Bu)-Pro on the carrier resin. Then, Steps (a)–(e) were repeated to obtain the carrier resin to which a protected peptide was bound. In Step (d) in the repeated procedures, Fmoc-Gly-OH, Fmoc-Ser(t-Bu)-OH, Fmoc-Gly-OH, Fmoc-Thr(t-Bu)-OH, Fmoc-Asn(Trt)-OH, Fmoc-Thr(t-Bu)-OH, Fmoc-Arg(Pmc)-OH, Fmoc-Pro-OH, Fmoc-Tyr(t-Bu)-OH, Fmoc-Thr(t-Bu)-OH, Fmoc-Gln(Trt)-OH, Fmoc-Leu-OH, Fmoc-Lys(Boc)-OH, Fmoc-His(Trt)-OH, Fmoc-Leu-OH, Fmoc-Glu(Ot-Bu)-OH, Fmoc-Gln(Trt)-OH, Fmoc-Ser(t-Bu)-OH, Fmoc-Leu-OH, Fmoc-Lys(Boc)-OH, Fmoc-Gly-OH, and Fmoc-Leu-OH were used in turn. Further, the washing and deprotection steps (a)–(c) were carried out, followed by washing with methanol and butyl ether in turn. The resulting resin was dried for 12 hours under reduced pressure to give 240 mg of the carrier resin to which a side-chain-protected peptide was bound. To 40 mg of this carrier resin was added 200 μl of a mixture of TFA (82.5%), thioanisole (5%), water (5%), ethyl methyl sulfide (3%), 1,2-ethanedithiol (2.5%) and thiophenol (2%), and the resulting mixture was left to stand at room temperature for 8 hours to remove the side-chain-protecting groups and to cleave the peptide from the resin. After the resin was separated by filtration, about 10 ml of ether was added to the filtrate, and the deposited precipitate was collected by centrifugation and decantation to give 25.6 mg of a crude peptide. This crude product was purified by HPLC in the same manner as in Step 2 of Reference Example 1 to give 3.8 mg of Compound 17; (SEQ ID NO: 21)

Mass spectrum [FABMS]: 2624 (M+H)

Amino acid analysis: Asx 0.9 (1), Glx 2.9 (3), Ser 2.0 (2), Gly 3.2 (3), His 1.0 (1), Arg 1.0 (1), Thr 3.7 (4), Pro 1.9 (2), Tyr 0.9 (1), Leu 4.0 (4), Lys 1.8 (2)

REFERENCE EXAMPLE 4

Synthesis of Compound 18 (H-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro-$NH_2$; SEQ ID NO: 22)

DMF (297.5 μl) containing 85 μmol of Fmoc-Val-OH, 85 μmol of PyBOP, 85 μmol of HOBt and 127.5 μmol of NMM was stirred for 3 minutes. The obtained solution was added to 80 mg of the resin to which the peptide was bound as obtained in Reference Example 3. The mixture was stirred for 30 minutes and the solution was discharged. After the treatments of Steps (a), (b) and (c) of Reference Example 3 were carried out, the resin was washed and dried in the same manner as in Reference Example 3 to give 81 mg of the carrier resin to which a side-chain-protected peptide was bound. Then, 27 mg of the obtained resin was subjected to cleavage of the peptide and purification by HPLC in the same manner as in Reference Example 3 to give 2.6 mg of Compound d.

Mass spectrum [FABMS]: 2723 (M+H)

Amino acid analysis: Asx 0.6 (1), Glx 2.7 (3), Ser 2.0 (2), Gly 3.4 (3), His 1.0 (1), Arg 1.1 (1), Thr 3.3 (4), Pro 2.2 (2), Tyr 1.1 (1), Val 0.9 (1), Leu 4.0 (4), Lys 2.0 (2), Trp was not analyzed.

REFERENCE EXAMPLE 5

Synthesis of Compound 19 (H-Val-Leu-Ala-Ala-Leu-Ala-Ala-Ala-Leu-Ala-Ala-Leu-Ala-Ala-Leu-Pro-Arg-Thr-Asn-Thr-Gly-Ser-Gly-Thr-Pro-$NH_2$; SEQ ID NO: 23)

A carrier resin to which a side-chain-protected peptide was bound (68.2 mg) was obtained in the same manner as in Reference Example 3 using 30 mg of a carrier resin to which 14.1 μmol of Fmoc-NH was bound as the starting material, and using Fmoc-Pro-OH, Fmoc-Thr(t-Bu)-OH, Fmoc-Gly-OH, Fmoc-Ser(t-Bu)-OH, Fmoc-Gly-OH, Fmoc-Thr(t-Bu)-OH, Fmoc-Asn(Trt)-OH, Fmoc-Thr(t-Bu)-OH, Fmoc-Arg (Pmc)-OH, Fmoc-Pro-OH, Fmoc-Leu-OH, Fmoc-Ala-OH, Fmoc-Ala-OH, Fmoc-Leu-OH, Fmoc-Ala-OH, Fmoc-Ala-OH, Fmoc-Leu-OH, Fmoc-Ala-OH, Fmoc-Ala-OH, Fmoc-Ala-OH, Fmoc-Leu-OH, Fmoc-Ala-OH, Fmoc-Ala-OH, Fmoc-Leu-OH, and Fmoc-Val-OH in turn. Then, 22.7 mg of the obtained resin was subjected to cleavage of the peptide and purification by HPLC in the same manner as in Reference Example 3 to give 1.1 mg of Compound e. As the reversed-phase column, YMC column (YMC-Pack ODS-AM SH343-5 20 mm I.D. ×250 mm) was used.

Mass spectrum [FABMS]: 2289 (M+H)

Amino acid analysis: Asx 1.0 (1), Ser 1.2 (1), Gly 2.4 (2), Arg 1.1 (1), Thr 3.0 (3), Pro 2.1 (2), Ala 8.8 (9), Val 0.7 (1), Leu 5.0 (5)

REFERENCE EXAMPLE 6

Synthesis of Compound 20 (H-Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro-$NH_2$; SEQ ID NO: 24)

A carrier resin to which a protected peptide was bound (141.5 mg) was obtained in the same manner as in Reference Example 3 using 50 mg of a carrier resin to which 23.5 μmol of Fmoc-NH was bound as the starting material, and using Fmoc-Pro-OH, Fmoc-Ala-OH, Fmoc-Gly-OH, Fmoc-Val-OH, Fmoc-Gly-OH, Fmoc-Ile-OH, Fmoc-Ala-OH, Fmoc-Thr(t-Bu)-OH, Fmoc-Gln(Trt)-OH, Fmoc-Pro-OH, Fmoc-Phe-OH, Fmoc-Thr(t-Bu)-OH, Fmoc-His(Trt)-OH, Fmoc-Phe-OH, Fmoc-Lys(Boc)-OH, Fmoc-Asn(Trt)-OH, Fmoc-Phe-OH, Fmoc-Asp(Ot-Bu)-OH, Fmoc-Gln(Trt)-OH, Fmoc-Thr(t-Bu)-OH, Fmoc-Tyr(t-Bu)-OH, Fmoc-Thr(t-Bu)-OH, Fmoc-Gly-OH, Fmoc-Leu-OH, and Fmoc-Met-OH in turn. Then, 48 mg of the obtained resin was subjected to cleavage of the peptide and purification by HPLC in the same manner as in Reference Example 3 to give 8.4 mg of Compound f.

Mass spectrum [FABMS]: 2739 (M+H)

Amino acid analysis: Asx 2.0 (2), Glx 2.0 (2), Gly 3.2 (3), His 1.0 (1), Thr 3.9 (4), Ala 2.0 (2), Pro 2.0 (2), Tyr 0.9 (1), Val 1.0 (1), Met 0.9 (1), Ile 1.0 (1), Leu 1.0 (1), Phe 2.8 (3), Lys 1.0 (1)

REFERENCE EXAMPLE 7

Synthesis of Compound 21 (H-Gly-Leu-Gly-Ser-Leu-Thr-Glu-Val-Leu-Ala-Lys-Leu-Ala-Ala-Tyr-Pro-Arg-Thr-Asn-Thr-Gly-Ser-Gly-Thr-Pro-$NH_2$; SEQ ID NO: 25)

A carrier resin to which a protected peptide was bound (51.9 mg) was obtained in the same manner as in Reference Example 3 using 20 mg of a carrier resin to which 9.4 μmol of Fmoc-NH was bound as the starting material, and using Fmoc-Pro-OH, Fmoc-Thr(t-Bu)-OH, Fmoc-Gly-OH, Fmoc-Ser(t-Bu)-OH, Fmoc-Gly-OH, Fmoc-Thr(t-Bu)-OH, Fmoc-Asn(Trt)-OH, Fmoc-Thr(t-Bu)-OH, Fmoc-Arg(Pmc)-OH, Fmoc-Pro-OH, Fmoc-Tyr(t-Bu)-OH, Fmoc-Ala-OH, Fmoc-Ala-OH, Fmoc-Leu-OH, Fmoc-Lys(Boc)-OH, Fmoc-Ala-OH, Fmoc-Leu-OH, Fmoc-Val-OH, Fmoc-Glu(t-Bu)-OH, Fmoc-Thr(t-Bu)-OH, Fmoc-Leu-OH, Fmoc-Ser(t-Bu)-OH, Fmoc-Gly-OH, Fmoc-Leu-OH, and Fmoc-Gly-OH in turn. Then, 17.3 mg of the obtained resin was subjected to cleavage of the peptide and purification by HPLC in the same manner as in Reference Example 3 to give 3.6 mg of Compound g. As the reversed-phase column, YMC column (YMC-Pack ODS-AM SH343-5 20 mm I.D. ×250 mm) was used.

Mass spectrum [FABMS]: 2471 (M+H)

Amino acid analysis: Asx 0.9 (1), Glx 1.0 (1), Ser 1.9 (2), Gly 3.9 (4), Arg 1.0 (1), Thr 3.8 (4), Ala 2.8 (3), Pro 1.9 (2), Tyr 0.9 (1), Val 0.9 (1), Leu 4.0 (4), Lys 1.0 (1)

REFERENCE EXAMPLE 8

Synthesis of Compound 22 (H-Gly-Leu-Gly-Ser-Leu-Thr-Glu-Val-Leu-Ala-Lys-Leu-Ala-Ala-Tyr-Pro-Arg-Ser-Gln-Thr-Gly-Ala-Gly-Thr-Pro-$NH_2$; SEQ ID NO: 26)

A carrier resin to which a protected peptide was bound (52.3 mg) was obtained in the same manner as in Reference Example 3 using 20 mg of a carrier resin to which 9.4 μmol of Fmoc-NH was bound as the starting material, and using Fmoc-Pro-OH, Fmoc-Thr(t-Bu)-OH, Fmoc-Gly-OH, Fmoc-Ala-OH, Fmoc-Gly-OH, Fmoc-Thr(t-Bu)-OH, Fmoc-Gln (Trt)-OH, Fmoc-Ser(t-Bu)-OH, Fmoc-Arg(Pmc)-OH, Fmoc-Pro-OH, Fmoc-Tyr(t-Bu)-OH, Fmoc-Ala-OH, Fmoc-Ala-OH, Fmoc-Leu-OH, Fmoc-Lys(Boc)-OH, Fmoc-Ala-OH, Fmoc-Leu-OH, Fmoc-Val-OH, Fmoc-Glu(t-Bu)-OH, Fmoc-Thr(t-Bu)-OH, Fmoc-Leu-OH, Fmoc-Ser(t-Bu)-OH, Fmoc-Gly-OH, Fmoc-Leu-OH, and Fmoc-Gly-OH in turn. Then, 17.1 mg of the obtained resin was subjected to cleavage of the peptide and purification by HPLC in the same manner as in Reference Example 3 to give 2.4 mg of Compound h. As the reversed-phase column, YMC column (YMC-Pack ODS-AM SH343-5 20 mm I.D. ×250 mm) was used.

Mass spectrum [FABMS]: 2456 (M+H)

Amino acid analysis: Glx 1.9 (2), Ser 1.9 (2), Gly 4.0 (4), Arg 1.0 (1), Thr 2.9 (3), Ala 3.9 (4), Pro 1.9 (2), Tyr 0.9 (1), Val 0.8 (1), Leu 4.0 (4), Lys 1.0 (1)

REFERENCE EXAMPLE 9

Synthesis of Compound 23 (H-Gly-Leu-Gly-Ser-Leu-Thr-Glu-Val-Leu-Ala-Lys-Leu-Ala-Ala-Tyr-Hyp-Arg-Thr-Asn-Thr-Gly-Ser-Gly-Thr-Hyp-$NH_2$; SEQ ID NO: 27)

A carrier resin to which a protected peptide was bound (54.7 mg) was obtained in the same manner as in Reference Example 3 using 20 mg of a carrier resin to which 9.4 μmol of Fmoc-NH was bound as the starting material, and using Fmoc-Hyp(t-Bu)-OH, Fmoc-Thr(t-Bu)-OH, Fmoc-Gly-OH, Fmoc-Ser(t-Bu)-OH, Fmoc-Gly-OH, Fmoc-Thr(t-Bu)-OH, Fmoc-Asn(Trt)-OH, Fmoc-Thr(t-Bu)-OH, Fmoc-Arg(Pmc)-OH, Fmoc-Hyp(t-Bu)-OH, Fmoc-Tyr(t-Bu)-OH, Fmoc-Ala-OH, Fmoc-Ala-OH, Fmoc-Leu-OH, Fmoc-Lys(Boc)-OH, Fmoc-Ala-OH, Fmoc-Leu-OH, Fmoc-Val-OH, Fmoc-Glu(t-Bu)-OH, Fmoc-Thr(t-Bu)-OH, Fmoc-Leu-OH, Fmoc-Ser(t-Bu)-OH, Fmoc-Gly-OH, Fmoc-Leu-OH, and Fmoc-Gly-OH in turn. Then, 18.2 mg of the obtained resin was subjected to cleavage of the peptide and purification by HPLC in the same manner as in Reference Example 3 to give 2.9 mg of Compound 23. As the reversed-phase column, YMC column (YMC-Pack ODS-AM SH343-5 20 mm I.D.×250 mm) was used.

Mass spectrum [FABMS]: 2504 (M+H)

Amino acid analysis: Asx 1.0 (1), Glx 1.0 (1), Ser 2.0 (2), Gly 4.1 (4), Arg 1.0 (1), Thr 3.8 (4), Ala 3.0 (3), Tyr 1.0 (1), Val 0.8 (1), Leu 4.0 (4), Lys 0.9 (1), Hyp was not analyzed.

REFERENCE EXAMPLE 10

Synthesis of Compound 24 (H-Gly-Leu-Gly-Ser-Leu-Thr-Glu-Val-Leu-Ala-Lys-Leu-Ala-Ala-Tyr-Pro-Arg-Thr-Asn-Thr-β-Ala-Ser-Gly-Thr-Pro-$NH_2$; SEQ ID NO: 28)

A carrier resin to which a protected peptide was bound (55.4 mg) was obtained in the same manner as in Reference Example 3 using 20 mg of a carrier resin to which 9.4 μmol of Fmoc-NH was bound as the starting material, and using Fmoc-Pro-OH, Fmoc-Thr(t-Bu)-OH, Fmoc-Gly-OH, Fmoc-Ser(t-Bu)-OH, Fmoc-β-Ala-OH, Fmoc-Thr(t-Bu)-OH, Fmoc-Asn(Trt)-OH, Fmoc-Thr(t-Bu)-OH, Fmoc-Arg(Pmc)-OH, Fmoc-Pro-OH, Fmoc-Tyr(t-Bu)-OH, Fmoc-Ala-OH, Fmoc-Ala-OH, Fmoc-Leu-OH, Fmoc-Lys(Boc)-OH, Fmoc-Ala-OH, Fmoc-Leu-OH, Fmoc-Val-OH, Fmoc-Glu(t-Bu)-OH, Fmoc-Thr(t-Bu)-OH, Fmoc-Leu-OH, Fmoc-Ser(t-Bu)-OH, Fmoc-Gly-OH, Fmoc-Leu-OH, and Fmoc-Gly-OH in turn. Then, 18.1 mg of the obtained resin was subjected to cleavage of the peptide and purification by HPLC in the same manner as in Reference Example 3 to give 3.9 mg of Compound 24. As the reversed-phase column, YMC column (YMC-Pack ODS-AM SH343-5 20 mm I.D.×250 mm) was used.

Mass spectrum [FABMS]: 2486 (M+H)

Amino acid analysis: Asx 0.9 (1), Glx 1.0 (1), Ser 1.9 (2), Gly 3.0 (3), β-Ala 1.1 (1), Arg 1.0 (1), Thr 3.8 (4), Ala 2.9 (3), Pro 2.0 (2), Tyr 0.9 (1), Val 0.8 (1), Leu 4.0 (4), Lys 0.9 (1)

REFERENCE EXAMPLE 11

Synthesis of Compound 25 (H-Gly-Leu-Gly-Ser-Leu-Thr-Glu-Val-Leu-Ala-Lys-Leu-Ala-Glu-Tyr-Pro-Arg-Thr-Asn-Thr-Gly-Ser-Gly-Thr-Pro-$NH_2$; SEQ ID NO: 29)

A carrier resin to which a protected peptide was bound (80.3 mg) was obtained in the same manner as in Reference Example 3 using 30 mg of a carrier resin to which 14.1 μmol of Fmoc-NH was bound, and using Fmoc-Pro-OH, Fmoc-Thr(t-Bu)-OH, Fmoc-Gly-OH, Fmoc-Ser(t-Bu)-OH, Fmoc-Gly-OH, Fmoc-Thr(t-Bu)-OH, Fmoc-Asn(Trt)-OH, Fmoc-Thr(t-Bu)-OH, Fmoc-Arg(Pmc)-OH, Fmoc-Pro-OH, Fmoc-Tyr(t-Bu)-OH, Fmoc-Glu(Ot-Bu)-OH, Fmoc-Ala-OH, Fmoc-Leu-OH, Fmoc-Lys-(Boc)-OH, Fmoc-Ala-OH, Fmoc-Leu-OH, Fmoc-Val-OH, Fmoc-Glu(Ot-Bu)-OH, Fmoc-Thr(t-Bu)-OH, Fmoc-Leu-OH, Fmoc-Ser(t-Bu)-OH, Fmoc-Gly-OH, Fmoc-Leu-OH, and Fmoc-Gly-OH in turn. Then, 26.8 mg of the obtained resin was subjected to cleavage of the peptide and purification by HPLC in the same manner as in Reference Example 3 to give 3.0 mg of Compound k. As the reversed-phase column, YMC column (YMC-Pack ODS-AM SH343-5 20 mm I.D. ×250 mm) was used.

Mass spectrum [FABMS]: 2530 (M+H)

Amino acid analysis: Asx 0.8 (1), Glx 2.0 (2), Ser 1.9 (2), Gly 4.3 (4), Arg 1.0 (1), Thr 3.9 (4), Pro 2.1 (2), Ala 2.1 (1), Tyr 1.0 (1), Val 0.9 (1), Leu 4.0 (4), Lys 1.0 (1)

REFERENCE EXAMPLE 12

Synthesis of Compound 26 (H-Gly-Leu-Gly-Ser-Leu-Thr-Gla-Val-Leu-Ala-Lys-Leu-Ala-Glu-Tyr-Pro-Arg-Thr-Asn-Thr-Gly-Ser-Gly-Thr-Pro-$NH_2$; SEQ ID NO: 30)

A carrier resin to which a protected peptide was bound (82.1 mg) was obtained in the same manner as in Reference Example 3 using 30 mg of a carrier resin to which 14.1 μmol of Fmoc-NH was bound, and using Fmoc-Pro-OH, Fmoc-Thr(t-Bu)-OH, Fmoc-Gly-OH, Fmoc-Ser(t-Bu)-OH, Fmoc-Gly-OH, Fmoc-Thr(t-Bu)-OH, Fmoc-Asn (Trt)-OH, Fmoc-Thr(t-Bu)-OH, Fmoc-Arg(Pmc)-OH, Fmoc-Pro-OH, Fmoc-Tyr(t-Bu)-OH, Fmoc-Glu(Ot-Bu)-OH, Fmoc-Ala-OH, Fmoc-Leu-OH, Fmoc-Lys(Boc)-OH, Fmoc-Ala-OH, Fmoc-Leu-OH, Fmoc-Val-OH, Fmoc-Gla(Ot-Bu)2-OH, Fmoc-Thr (t-Bu)-OH, Fmoc-Leu-OH, Fmoc-Ser(t-Bu)-OH, Fmoc-Gly-OH, Fmoc-Leu-OH, and Fmoc-Gly-OH in turn. Then, 27.4 mg of the obtained resin was subjected to cleavage of the peptide and purification by HPLC in the same manner as in Reference Example 3 to give 3.6 mg of Compound 1. As the reversed-phase column, YMC column (YMC-Pack ODS-AM SH343-5 20 mm I.D. ×250 mm) was used.

Mass spectrum [FABMS]: 2574 (M+H)

Amino acid analysis: Asx 0.8 (1), Glx 2.1 (2), Ser 2.0 (2), Gly 4.3 (4), Arg 1.0 (1), Thr 4.1 (4), Pro 2.0 (2), Ala 2.1 (2), Tyr 1.0 (1), Val 0.9 (1), Leu 4.0 (4), Lys 1.0 (1), Gla was detected as Glx.

REFERENCE EXAMPLE 13

Synthesis of Compound 27 (H-Gly-Leu-Gly-Ser-Leu-Thr-Glu-Val-Leu-Ala-Lys-Leu-Ala-Gla-Tyr-Pro-Arg-Thr-Asn-Thr-Gly-Ser-Gly-Thr-Pro-$NH_2$; SEQ ID NO: 31)

A carrier resin to which a protected peptide was bound (46.8 mg) was obtained in the same manner as in Reference Example 3 using 30 mg of a carrier resin to which 14.1 μmol of Fmoc-NH was bound, and using Fmoc-Pro-OH, Fmoc-Thr(t-Bu)-OH, Fmoc-Gly-OH, Fmoc-Ser(t-Bu)-OH, Fmoc-Gly-OH, Fmoc-Thr(t-Bu)-OH, Fmoc-Asn(Trt)-OH, Fmoc-Thr(t-Bu)-OH, Fmoc-Arg(Pmc)-OH, Fmoc-Pro-OH, Fmoc-Tyr(t-Bu)-OH, Fmoc-Gla(Ot-Bu)2-OH, Fmoc-Ala-OH, Fmoc-Leu-OH, Fmoc-Lys(Boc)-OH, Fmoc-Ala-OH, Fmoc-Leu-OH, Fmoc-Val-OH, Fmoc-Glu(Ot-Bu)-OH, Fmoc-Thr (t-Bu)-OH, Fmoc-Leu-OH, Fmoc-Ser(t-Bu)-OH, Fmoc-Gly-OH, Fmoc-Leu-OH, and Fmoc-Gly-OH in turn. Then, 15.6 mg of the obtained resin was subjected to cleavage of the peptide and purification by HPLC in the same manner as in Reference Example 3 to give 0.8 mg of Compound m. As the reversed-phase column, YMC column (YMC-Pack ODS-AM SH343-5 20 mm I.D. ×250 mm) was used.

Mass spectrum [FABMS]: 2574 (M+H)

Amino acid analysis: Asx 0.9 (1), Glx 2.1 (2), Ser 1.8 (2), Gly 3.9 (4), Arg 1.0 (1), Thr 3.5 (4), Pro 1.7 (2), Ala 2.1 (2), Tyr 1.0 (1), Val 0.9 (1), Leu 4.0 (4), Lys 0.9 (1), Gla was detected as Glx.

REFERENCE EXAMPLE 14

Synthesis of Compound 28; (SEQ ID NO: 32) (H-Gly-Leu-Gly-Ser-Leu-Thr-Glu-Val-Leu-Ala-Lys-Leu-Ala-Glu-Tyr-Pro-Arg-Thr-Asn-Thr-Gly-Ser-Gly-Thr-Pro-β-Ala

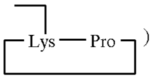

Four pinheads to which a protected peptide was bound were obtained in the same manner as in Reference Example 3, using 4 synthesis pinheads of a multipin peptide synthesis kit (Cleavable Peptide Kit-Diketopiperazine C-termini) of Chiron Mimotopes Pty. Ltd. (Australia) instead of the carrier resin in Reference Example 3, and using Fmoc-Pro-OH, Fmoc-Thr(t-Bu)-OH, Fmoc-Gly-OH, Fmoc-Ser(t-Bu)-OH, Fmoc-Gly-OH, Fmoc-Thr(t-Bu)-OH, Fmoc-Asn(Trt)-OH, Fmoc-Thr(t-Bu)-OH, Fmoc-Arg(Pmc)-OH, Fmoc-Pro-OH, Fmoc-Tyr(t-Bu)-OH, Fmoc-Glu(Ot-Bu)-OH, Fmoc-Ala-OH, Fmoc-Leu-OH, Fmoc-Lys(Boc)-OH, Fmoc-Ala-OH, Fmoc-Leu-OH, Fmoc-Val-OH, Fmoc-Glu(Ot-Bu)-OH, Fmoc-Thr(t-Bu)-OH, Fmoc-Leu-OH, Fmoc-Ser(t-Bu)-OH, Fmoc-Gly-OH, Fmoc-Leu-OH, and Fmoc-Gly-OH in turn. Then, two of the obtained pinheads were subjected to the same treatment as in the cleavage of the peptide in Reference Example 3 to remove the side-chain-protecting groups. After discharge of the solution, the pinheads were washed with methanol and dried under reduced pressure to give the pinheads to which a peptide free from the side-chain-protecting groups was bound. To these pinheads was added 0.5 ml of 0.05 M HEPES buffer (pH 8.2), and the resulting mixture was left to stand at room temperature for 5 hours to cleave the peptide from the pinheads. The resulting solution containing the peptide was purified by HPLC in the same manner as in Reference Example 3 to give 0.26 mg of Compound n. As the reversed-phase column, YMC column (YMC-Pack ODS-AM SH343-5 20 mm I.D. ×250 mm) was used.

Mass spectrum [FABMS]: 2809 (M+H)

Amino acid analysis: Asx 0.7 (1), Glx 1.9 (2), Ser 1.9 (2), Gly 4.3 (4), Arg 1.1 (1), Thr 3.9 (4), Pro 3.1 (3), Ala 2.1 (2), Tyr 1.0 (1), Val 0.9 (1), Leu 4.0 (4), Lys 2.0 (2), β-Ala 1.2 (1)

REFERENCE EXAMPLE 15

Synthesis of Compound 29; (SEQ ID NO: 33) (H-Gly-Leu-Gly-Ser-Leu-Thr-Glu-Val-Leu-Ala-Lys-Leu-Ala-Glu-Tyr-Pro-D-Arg-Thr-Asn-Thr-Gly-Ser-Gly-Thr-Pro-$NH_2$)

A carrier resin to which a protected peptide was bound (74.7 mg) was obtained in the same manner as in Reference Example 3 using 30 mg of a carrier resin to which 14.1 μmol of Fmoc-NH was bound, and using Fmoc-Pro-OH, Fmoc-Thr(t-Bu)-OH, Fmoc-Gly-OH, Fmoc-Ser(t-Bu)-OH, Fmoc-Gly-OH, Fmoc-Thr(t-Bu)-OH, Fmoc-Asn(Trt)-OH, Fmoc-Thr(t-Bu)-OH, Fmoc-D-Arg(Pmc)-OH, Fmoc-Pro-OH, Fmoc-Tyr(t-Bu)-OH, Fmoc-Glu(Ot-Bu)-OH, Fmoc-Ala-OH, Fmoc-Leu-OH, Fmoc-Lys(Boc)-OH, Fmoc-Ala-OH, Fmoc-Leu-OH, Fmoc-Val-OH, Fmoc-Glu(Ot-Bu)-OH, Fmoc-Thr(t-Bu)-OH, Fmoc-Leu-OH, Fmoc-Ser(t-Bu)-OH, Fmoc-Gly-OH, Fmoc-Leu-OH, and Fmoc-Gly-OH in turn. Then, 24.9 mg of the obtained resin was subjected to cleavage of the peptide and purification by HPLC in the same manner as in Reference Example 3 to give 2.3 mg of Compound o.

Mass spectrum [FABMS]: 2530 (M+H)

Amino acid analysis: Asx 1.3 (1), Glx 2.4 (2), Ser 2.1 (2), Gly 4.3 (4), Arg 1.1 (1), Thr 4.4 (4), Pro 2.2 (2), Ala 1.7 (2), Tyr 1.1 (1), Val 1.1 (1), Leu 4.1 (4), Lys 1.2 (1)

REFERENCE EXAMPLE 16

Synthesis of Compound 30 (H-Gly-Leu-Gly-Ser-Leu-Thr-Glu-Val-Leu-Ala-Lys-Leu-Ala-Glu-Tyr-Pro-Lys-Thr-Asn-Thr-Gly-Ser-Gly-Thr-Pro-$NH_2$; SEQ ID NO: 16)

A carrier resin to which a protected peptide was bound (62.5 mg) was obtained in the same manner as in Reference Example 3 using 30 mg of a carrier resin to which 14.1 μmol of Fmoc-NH was bound, and using Fmoc-Pro-OH, Fmoc-Thr(t-Bu)-OH, Fmoc-Gly-OH, Fmoc-Ser(t-Bu)-OH, Fmoc-Gly-OH, Fmoc-Thr(t-Bu)-OH, Fmoc-Asn(Trt)-OH, Fmoc-Thr(t-Bu)-OH, Fmoc-Lys(Boc)-OH, Fmoc-Pro-OH, Fmoc-Tyr(t-Bu)-OH, Fmoc-Glu(Ot-Bu)-OH, Fmoc-Ala-OH, Fmoc-Leu-OH, Fmoc-Lys(Boc)-OH, Fmoc-Ala-OH, Fmoc-Leu-OH, Fmoc-Val-OH, Fmoc-Glu(Ot-Bu)-OH, Fmoc-Thr (t-Bu)-OH, Fmoc-Leu-OH, Fmoc-Ser(t-Bu)-OH, Fmoc-Gly-OH, Fmoc-Leu-OH, and Fmoc-Gly-OH in turn. Then, 20.8 mg of the obtained resin was subjected to cleavage of the peptide and purification by HPLC in the same manner as in Reference Example 3 to give 3.6 mg of Compound p.

Mass spectrum [FABMS]: 2502 (M+H)

Amino acid analysis: Asx 1.2 (1), Glx 2.4 (2), Ser 2.1 (2), Gly 4.3 (4), Thr 4.4 (4), Pro 2.2 (2), Ala 1.7 (2), Tyr 1.1 (1), Val 1.1 (1), Leu 4.1 (4), Lys 2.4 (2)

Industrial Applicability

The present invention provides novel calcitonin derivatives having higher biological activity and/or stability than calcitonin, partial calcitonin peptides, or analogues thereof.

We claim:

1. A compound represented by formula (I):

(I)

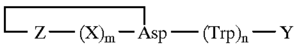

wherein Z represents Gly or Cys; X represents an α-amino acid residue; Y represents a natural calcitonin moiety or a natural calcitonin-like peptide moiety; the moiety represented by the following formula (II):

$$P^1\text{-}P^2\text{-Leu-}P^3\text{-}P^4\text{-}P^5\text{-}P^6\text{-}P^7\text{-}P^8\text{-}P^9\text{-}P^{10}\text{-}P^{11}\text{-}P^{12}\text{-}P^{13}\text{-}P^{14}\text{-}P^{15}\text{-}P^{16}\text{-}P^{17}\text{-Gly-}P^{18}\text{-}P^{11}\text{-}P^{19} \quad \text{(II)}$$

wherein $P^1$ represents a single bond, Cys-Gly-Asn-Leu-Ser-Thr-Cys, Ser-Gly-Asn-Leu-Ser-Thr-Ser, Cys-Ser-Asn-Leu-Ser-Thr-Cys or Ser-Ser-Asn-Leu-Ser-Thr-Ser; $P^2$ represents Val, Met, Gly or a single bond; $P^3$ represents Gly-Lys, Ala-Ala, Gly-Thr or Gly-Ser; $P^4$ represents Leu or Tyr; $P^5$ represents Ser-Gln-Glu, Ala-Ala-Ala, Thr-Gln-Asp, Thr-Glu-Val or Thr-Gla-Val; $P^6$ represents Leu or Phe; $P^7$ represents His-Lys, Ala-Ala, Asn-Lys or Ala-Lys; $P^8$ represents Gln, Ala or His; $P^9$ represents Thr, Ala, Glu or Gla; $P^{10}$ represents Tyr, Phe or Leu; $P^{11}$ represents Pro or Hyp; $P^{12}$ represents Arg, Gln, Lys or D-Arg; $P^{13}$ represents Thr or Ser; $P^{14}$ represents Asn, Gln or Ala; $P^{15}$ represents Thr or Ile; $P^{16}$ represents Gly or b-Ala; $P^{17}$ represents Ser, Val or Ala; $P^{18}$ represents Thr or Ala; and $P^{19}$ represents an amino group or a group represented by the following formula (III), (III)

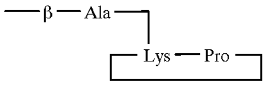

m represents an integer of 5–8, α-amino acid residues represented by X being the same or different; and n represents an integer of 0–3; provided that when m is 5, the sequence of 4 C-terminal residues of $—(X)_m—$ is different from the sequence of the third to sixth amino acids of natural calcitonin, and pharmaceutically acceptable salts thereof.

2. A compound according to claim 1, wherein $—(X)_m—$ in formula (I) are -$X^1$-Trp-$X_2$-Gly-Thr-Ala-$X^3$-(wherein $X^1$ represents Asn or Asp; $X^2$ represents His or Lys; and $X^3$ represents Pro or Ala), -Ser-Ala-Ala-Val-Tyr-Phe-, -Phe-Ile-Gly-Trp-Gly-Asn-, -Tyr-Pro-Trp-Trp-Asn-Tyr-Arg-, or -Leu-Gly-Val-Gly-Ser-$X^4$-Asn- (wherein $X^4$ represents Cys, Ala or Ser), and pharmaceutically acceptable salts thereof.

3. A compound according to claim 2, wherein said compounds have increased stability in the presence of prolylendopeptidase as compared to calcitonin.

* * * * *